US009777315B2

(12) United States Patent
Fredriksson et al.

(10) Patent No.: US 9,777,315 B2
(45) Date of Patent: Oct. 3, 2017

(54) EXONUCLEASE ENABLED PROXIMITY EXTENSION ASSAYS

(75) Inventors: Simon Fredriksson, Stockholm (SE); Martin Lundberg, Uppsala (SE); Anna Eriksson, Uppsala (SE); Emma Rennel-Dickens, Uppsala (SE)

(73) Assignee: OLINK PROTEOMICS AB, Uppsala (SE)

( * ) Notice: Subject to any disclaimer, the term of this patent is extended or adjusted under 35 U.S.C. 154(b) by 538 days.

(21) Appl. No.: 13/981,943

(22) PCT Filed: Jan. 30, 2012

(86) PCT No.: PCT/EP2012/051474
§ 371 (c)(1),
(2), (4) Date: Oct. 15, 2013

(87) PCT Pub. No.: WO2012/104261
PCT Pub. Date: Aug. 9, 2012

(65) Prior Publication Data
US 2014/0030721 A1 Jan. 30, 2014

(30) Foreign Application Priority Data
Jan. 31, 2011 (GB) .................................. 1101621.9

(51) Int. Cl.
*C12Q 1/68* (2006.01)
*C12P 19/34* (2006.01)
*G01N 33/542* (2006.01)
*G01N 33/558* (2006.01)

(52) U.S. Cl.
CPC ......... *C12Q 1/6848* (2013.01); *C12Q 1/6804* (2013.01); *C12Q 1/689* (2013.01); *G01N 33/542* (2013.01); *G01N 33/558* (2013.01); *C12Q 2600/16* (2013.01)

(58) Field of Classification Search
None
See application file for complete search history.

(56) References Cited

U.S. PATENT DOCUMENTS

| 4,336,173 | A | 6/1982 | Ugelstad |
| 4,683,195 | A | 7/1987 | Mullis et al. |
| 4,683,202 | A | 7/1987 | Mullis |
| 4,800,159 | A | 1/1989 | Mullis et al. |
| 4,883,867 | A | 11/1989 | Lee et al. |
| 4,965,188 | A | 10/1990 | Mullis et al. |
| 5,223,409 | A | 6/1993 | Ladner et al. |
| 5,271,099 | A | 12/1993 | Lin |
| 5,321,130 | A | 6/1994 | Yue et al. |
| 5,410,030 | A | 4/1995 | Yue et al. |
| 5,436,134 | A | 7/1995 | Haughland et al. |
| 5,438,119 | A | 8/1995 | Rutter et al. |
| 5,440,016 | A | 8/1995 | Blondelle et al. |
| 5,449,603 | A | 9/1995 | Nielson et al. |
| 5,463,564 | A | 10/1995 | Agrafiotis et al. |
| 5,512,462 | A | 4/1996 | Cheng |
| 5,525,735 | A | 6/1996 | Gallop et al. |
| 5,534,407 | A | 7/1996 | Tabor et al. |
| 5,541,061 | A | 7/1996 | Fodor et al. |
| 5,545,568 | A | 8/1996 | Ellman |
| 5,549,974 | A | 8/1996 | Holmes |
| 5,565,324 | A | 10/1996 | Still et al. |
| 5,571,698 | A | 11/1996 | Ladner et al. |
| 5,574,656 | A | 11/1996 | Agrafiotis et al. |
| 5,582,977 | A | 12/1996 | Yue et al. |
| 5,593,853 | A | 1/1997 | Chen et al. |

(Continued)

FOREIGN PATENT DOCUMENTS

| WO | 93/06240 A1 | 4/1993 |
| WO | 95/05399 A1 | 2/1995 |

(Continued)

OTHER PUBLICATIONS

Engish translation of Chinese article Tang et al. (2009) China Biotechnology vol. 29, No. 8, pp. 113-118 (all pages of English translation of the 6 page chinese original are provided.).*
Nilsson et al. (2002) Nucl. Acids Res. vol. 30, No. 14 e66.*
Tang Na, et al., The New Technique for Protein Analyses: Proximity Litigation Assay and Its Application, China Biotechnology, vol. 29, No. 8, pp. 113-118 (Aug. 31, 2009), with English Abstract on p. 118.
Official Action dated Jun. 26, 2014 from corresponding Chinese Application No. 201280006856.9, and English Translation of Official Action.
Schwarz et al, "Improved yields of long PCR products using gene 32 protein," Nucleic Acids Research 18(4):1079, (1990).
Holland, et al, "Detection of specific polymerase chain reaction product by utilizing the 5'→3' exonuclease activity of Thermus aquaticus DNA polynerase," Proceedings of the National Academy of Sciences of the United States of America 88:7276-7280, Aug. 1991.

(Continued)

*Primary Examiner* — David Thomas
(74) *Attorney, Agent, or Firm* — Porter Wright Morris & Arthur

(57) ABSTRACT

The present invention relates to a proximity probe based detection assay ("proximity assay") for an analyte in a sample, specifically a proximity probe extension assay (PEA), an in particular to an improvement in the method to reduce non-specific "background" signals, wherein the improvement comprises the use in such assays of a component comprising 3' exonuclease activity, said method comprising: (a) contacting said sample with at least one set of at least first and second proximity probes, which probes each comprise an analyte-binding domain and a nucleic acid domain and can simultaneously bind to the analyte; (b) allowing the nucleic acid domains of the proximity probes to interact with each other upon binding of said proximity probes to said analyte, wherein said interaction comprises the formation of a duplex; (c) contacting said sample with a component comprising 3' exonuclease activity; (d) extending the 3' end of at least one nucleic acid domain of said duplex to generate an extension product, wherein the step may occur contemporaneously with or after step (c); and (e) amplifying and detecting the extension product.

52 Claims, 8 Drawing Sheets

(56) References Cited

U.S. PATENT DOCUMENTS

| | | | |
|---|---|---|---|
| 5,639,603 A | 6/1997 | Dower et al. | |
| 5,641,862 A | 6/1997 | Rutter et al. | |
| 5,658,751 A | 8/1997 | Yue et al. | |
| 5,684,711 A | 11/1997 | Agrafiotis et al. | |
| 5,688,696 A | 11/1997 | Lebl | |
| 5,688,997 A | 11/1997 | Baldwin et al. | |
| 5,698,673 A | 12/1997 | Blondelle et al. | |
| 5,708,153 A | 1/1998 | Dower et al. | |
| 5,721,099 A | 2/1998 | Still et al. | |
| 5,731,423 A | 3/1998 | Kaharla et al. | |
| 5,733,523 A | 3/1998 | Kuijpers et al. | |
| 5,734,018 A | 3/1998 | Rutter et al. | |
| 5,741,713 A | 4/1998 | Brown et al. | |
| 5,851,829 A | 12/1998 | Marasco et al. | |
| 5,863,753 A | 1/1999 | Haugland et al. | |
| 5,965,371 A | 10/1999 | Marasco et al. | |
| 5,989,823 A | 11/1999 | Jayasena et al. | |
| 6,117,635 A | 9/2000 | Nazarenko et al. | |
| 6,183,960 B1 | 2/2001 | Lizardi | |
| 6,210,884 B1 | 4/2001 | Lizardi | |
| 6,248,526 B1 | 6/2001 | Weimer | |
| 6,326,145 B1 | 12/2001 | Whitcombe et al. | |
| 6,511,809 B2 | 1/2003 | Baez et al. | |
| 6,558,928 B1 | 5/2003 | Landegren | |
| 7,659,069 B2 | 2/2010 | Belyaev et al. | |
| 7,932,060 B2 | 4/2011 | Nadeau et al. | |
| 2003/0152932 A1 | 8/2003 | Kumar et al. | |
| 2005/0009050 A1 | 1/2005 | Nadeau et al. | |
| 2005/0221349 A1 | 10/2005 | Wilson et al. | |
| 2008/0090238 A1 | 4/2008 | Yang et al. | |
| 2009/0061426 A1 | 3/2009 | Belyaev et al. | |
| 2009/0162840 A1 | 6/2009 | Fredriksson et al. | |

FOREIGN PATENT DOCUMENTS

| | | | |
|---|---|---|---|
| WO | 97/00446 A1 | 1/1997 | |
| WO | 98/37186 A1 | 8/1998 | |
| WO | 98/54312 A1 | 12/1998 | |
| WO | 01/61037 A1 | 8/2001 | |
| WO | 03/044231 A1 | 5/2003 | |
| WO | 2005/123963 A2 | 12/2005 | |
| WO | 2006/137932 A2 | 12/2006 | |
| WO | 2007/005649 A2 | 1/2007 | |
| WO | 2007/107743 A1 | 9/2007 | |
| WO | 2009/012220 A2 | 1/2009 | |
| WO | 2009/021031 A2 | 2/2009 | |
| WO | 2009/045906 A2 | 4/2009 | |
| WO | 2012/007511 A1 | 1/2012 | |

OTHER PUBLICATIONS

Lundberg et al, "High-fidelity amplification using a thermostable DNA polymerase isolated from Pyrococcus furiosus," Gene, 108:1-6, (1991).

Perler et al, "Intervening sequences in an Archaea DNA Polymerase gene," Proceedings of the National Academy Sciences of the United States of America 89:5577-5581, Jun. 1992.

Lee et al, "Allelic discrimination by nick-translation PCR with fluorogenic probes," Nucleic Acids Research 21(16):3761-3766 (1993).

Barnes, "PCR amplification of up to 35-kb DNA with high fidelity and high yield from λ bacteriophage templates," Proceedings of the National Academy of Sciences of the United States of America 91:2216-2220, Mar. 1994.

Heid et al, "Real Time Quantitative PCR," Genome Research 6:986-994 (1994).

Huang et al, "Fidelity and Predominant Mutations Produced by Deep Vent Wild-Type and Exonuclease-Deficient DNA Polymerases During In Vitro DNA Amplification," DNA and Cell Biology 15(7):589-594 (1996).

Hanes et al, "In Vitro selection and evolution of functional proteins by using ribosome display," Proceedings of the National Academy of Sciences of the United States of America 94:4937-4942, May 1997.

Nazarenko et al, "A closed tube format for amplification and detection of DNA based on energy transfer," Nucleic Acids Research 25(12):2516-2521 (1997).

Whitcombe et al, "Detection of PCR products using self-probing amplicons and fluorescence," Nature Biotechnology 17:804-807, Aug. 1999.

Roberts, "Totally in vitro protein selection using mRNA-protein fusions and ribosome display," Current Opinion in Chemical Biology 3:268-273 (1999).

Schaffitzel et al, "Ribosome display: An in vitro method for selection and evolution of antibodies from libraries," Journal of Immunological Methods 231:119-135 (1999).

Fitzgerald, "In vitro display technologies—new tools for drug discovery," Drug Discovery Today 5(6):253-258, Jun. 2000.

Kaboev et al, "PCR hot start using primers with the structure of molecular beacons (hairpin-like structure)," Nucleic Acids Research 28(21, e94):1-2 (2000).

Fredriksson et al, "Protein detection using proximity-dependent DNA ligation assays," Nature Biotechnology, 20:473-477, May 2002.

Gullberg et al, "Cytokine detection by antibody-based proximity ligation," PNAS, 101(22):8420-8424, Jun. 1, 2004.

Di Giusto et al, "Proximity extension of circular DNA aptamers with real-time protein detection," Nucleic Acids Research, 33(6, e64):1-7, Published online Apr. 7, 2005.

Search Report from corresponding GB 1101621.9 dated May 31, 2011.

Lundberg et al., Homogeneous antibody-based proximity extension assays provide sensitive and specific detection of low-abundant proteins in human blood, Nucleic Acids Research, vol. 39, No. 15, Jun. 6, 2011.

Weibrecht et al., Proximity ligation assays: A recent addition to the proteomics toolbox, Expert Review of Proteomics, vol. 7, No. 3, pp. 401-409, Jun. 1, 2010.

Soderberg et al., Characterizing proteins and their interactions in cells and tissue using the in situ proximity ligation assay, Methods, vol. 45, No. 3, pp. 227-232, Jul. 1, 2008.

Landegren et al., Molecular tools for a molecular medicine: Analyzing genes, transcripts and proteins using padlock and proximity probes, Journal of Molecular Recognition, vol. 17, No. 3, pp. 194-197, May 1, 2004.

Landegren et al., Padlock and proximity probes for in situ and array-based analyses: Tools for the post-genomic era, Comparative and Functional Genomics, vol. 4, No. 5, pp. 525-530, Oct. 1, 2003.

\* cited by examiner

```
                        SEQUENCE LISTING

<160> NUMBER OF SEQ ID NOS: 7

<210> SEQ ID NO 1
<211> LENGTH: 40
<212> TYPE: DNA
<213> ORGANISM: Artificial Sequence
<220> FEATURE:
<223> OTHER INFORMATION: Proximity probe nucleic acid domain

<400> SEQUENCE: 1
ggcccaagtg ttaatttgct tcacgatgag actggatgaa                              40

<210> SEQ ID NO 2
<211> LENGTH: 40
<212> TYPE: DNA
<213> ORGANISM: Artificial Sequence
<220> FEATURE:
<223> OTHER INFORMATION: Proximity probe nucleic acid domain

<400> SEQUENCE: 2
tcacggtagc ataaggtgca gtatgagaac ttcgctacag                              40

<210> SEQ ID NO 3
<211> LENGTH: 31
<212> TYPE: DNA
<213> ORGANISM: Artificial Sequence
<220> FEATURE:
<223> OTHER INFORMATION: qPCR primer Forward

<400> SEQUENCE: 3
tcgtgagccc aagtgttaat ttgcttcacg a                                       31

<210> SEQ ID NO 4
<211> LENGTH: 30
<212> TYPE: DNA
<213> ORGANISM: Artificial Sequence
<220> FEATURE:
<223> OTHER INFORMATION: qPCR primer Reverse

<400> SEQUENCE: 4
tgcagtctgt agcgaagttc tcatactgca                                         30

<210> SEQ ID NO 5
<211> LENGTH: 42
<212> TYPE: DNA
<213> ORGANISM: Artificial Sequence
<220> FEATURE:
<223> OTHER INFORMATION: qPCR Molecular Beacon
<220> FEATURE:
<221> NAME/KEY: modified_base
<222> LOCATION: (1)..(1)
<223> OTHER INFORMATION: Labelled with 6-carboxy-fluorescine
<220> FEATURE:
<221> NAME/KEY: modified_base
<222> LOCATION: (42)..(42)
<223> OTHER INFORMATION: Labelled with DABSYL

<400> SEQUENCE: 5
cccgctcgct tatgctaccg tgacctgcga atcccgagcg gg                           42
```

```
<210> SEQ ID NO 6
<211> LENGTH: 31
<212> TYPE: DNA
<213> ORGANISM: Artificial Sequence
<220> FEATURE:
<223> OTHER INFORMATION: qPCR Primer Forward
<220> FEATURE:
<221> NAME/KEY: modified_base
<222> LOCATION: (30)..(31)
<223> OTHER INFORMATION: Thioate modified

<400> SEQUENCE: 6
tcgtgagccc aagtgttaat ttgcttcacg a                              31

<210> SEQ ID NO 7
<211> LENGTH: 30
<212> TYPE: DNA
<213> ORGANISM: Artificial Sequence
<220> FEATURE:
<223> OTHER INFORMATION: qPCR Primer Reverse
<220> FEATURE:
<221> NAME/KEY: modified_base
<222> LOCATION: (29)..(30)
<223> OTHER INFORMATION: Thioate modified

<400> SEQUENCE: 7
tgcagtctgt agcgaagttc tcatactgca                                30
```

EXONUCLEASE ENABLED PROXIMITY EXTENSION ASSAYS

The present invention relates to a proximity probe based detection assay ("proximity assay") for an analyte in a sample, specifically a proximity probe extension assay (PEA). In particular, the present invention relates to an improvement in the method to reduce non-specific "background" signals which arise in all sample types, and can be particularly problematic in complex biological samples. The improvement comprises the use in such assays of a component comprising 3' exonuclease activity.

In proximity probe extension assays proximity probes are used, which bind to the analyte and have nucleic acid domains (or tags), that interact in a proximity-dependent manner upon said analyte binding. The interaction, generally via the formation of one or more nucleic acid duplexes (through the hybridisation of the nucleic acid domains), enables at least one of the nucleic acid domains to be extended from its 3' end. This extension product forms a detectable, preferably amplifiable, nucleic acid detection product, or detection tag, by means of which said analyte may be detected.

In the present invention the component comprising 3' exonuclease activity is added before or contemporaneously with component necessary for the extension of the nucleic acid domain(s), e.g. a polymerase enzyme. Thus, it is believed that the component comprising 3' exonuclease activity is able to degrade nucleic acid domains with a free and unprotected 3' end, i.e. domains on proximity probes that are not bound to the target analyte and therefore do not form a specific interaction or duplex. In the present invention the observable effect of the inclusion of a component comprising 3' exonuclease activity is to prevent the production of non-specific extension products from non-hybridised or "non-duplexed" nucleic acid domains, thereby increasing both the specificity and sensitivity of the assay. The present invention also provides a kit comprising a component comprising 3' exonuclease activity for use in the methods of the invention.

In general, a proximity assay relies on the principle of "proximity probing", wherein an analyte is detected by the binding of multiple (i.e. two or more, generally two or three) probes, which when brought into proximity by binding to the analyte (hence "proximity probes") allow a signal to be generated. Typically, at least one of the proximity probes comprises a nucleic acid domain (or moiety) linked to the analyte-binding domain (or moiety) of the probe, and generation of the signal involves an interaction between the nucleic acid moieties and/or a further functional moiety which is carried by the other probe(s). Thus signal generation is dependent on an interaction between the probes (more particularly between the nucleic acid or other functional moieties/domains carried by them) and hence only occurs when both the necessary (or more) probes have bound to the analyte, thereby lending improved specificity to the detection system. The concept of proximity probing has been developed in recent years and many assays based on this principle are now well known in the art. For example, "proximity probe extension assays" or "proximity extension assays" (PEA) refer to a specific type of assay, which utilises the extension of a nucleic acid domain, i.e. the templated addition of nucleotides to the end of a nucleic acid molecule, to generate a detectable signal.

Proximity-probe based detection assays, and particularly proximity extension assays permit the sensitive, rapid and convenient detection or quantification of one or more analytes in a sample by converting the presence of such an analyte into a readily detectable or quantifiable nucleic acid-based signal, and can be performed in homogeneous or heterogeneous formats.

Proximity probes of the art are generally used in pairs, and individually consist of an analyte-binding domain with specificity to the target analyte, and a functional domain, e.g. a nucleic acid domain coupled thereto. The analyte-binding domain can be for example a nucleic acid "aptamer" (Fredriksson et al (2002) Nat Biotech 20:473-477) or can be proteinaceous, such as a monoclonal or polyclonal antibody (Gullberg et al (2004) Proc Natl Acad Sci USA 101:8420-8424). The respective analyte-binding domains of each proximity probe pair may have specificity for different binding sites on the analyte, which analyte may consist of a single molecule or a complex of interacting molecules, or may have identical specificities, for example in the event that the target analyte exists as a multimer. When a proximity probe pair come into close proximity with each other, which will primarily occur when both are bound to their respective sites on the same analyte molecule, the functional domains (e.g. nucleic acid domains) are able to interact. In the context of the present invention, for example, nucleic acid domains may contain regions of complementarity to each other and hence the nucleic acid domains of the proximity probe pair may hybridise to form a duplex. One or more of the domains may be extended to form a new nucleic acid sequence, generally by means of a polymerisation reaction templated by the nucleic acid domain of the other proximity probe. The new nucleic acid sequence thereby generated serves to report the presence or amount of analyte in a sample, and can be qualitatively or quantitatively detected, for example by realtime, quantitative PCR (q-PCR).

Many variations of proximity probe based assays exist. For example, proximity extension assays are described in WO 01/61037, U.S. Pat. No. 6,511,809 and WO 2006/137932 and both heterogeneous (i.e. the analyte is first immobilised to a solid substrate by means of a specific analyte-binding reagent) and homogeneous (i.e. in solution) formats for proximity probe based assays have been disclosed, e.g. WO 01/61037, WO 03/044231, WO 2005/123963, Fredriksson et al (2002) Nat Biotech 20:473-477 and Gullberg et al (2004) Proc Natl Acad Sci USA 101: 8420-8424.

Although pairs of proximity probes are generally used, modifications of the proximity-probe detection assay have been described, in e.g. WO 01/61037, WO 2005/123963 and WO 2007/107743, where three proximity probes are used to detect a single analyte molecule. For example, the third proximity probe may be used to provide a further nucleic acid domain that can interact with nucleic acid domains of the first two proximity probes.

In addition to modification to the proximity-probe detection assay, modifications of the structure of the proximity probes themselves have been described, in e.g. WO 03/044231, where multivalent proximity probes are used. Such multivalent proximity probes comprise at least two, but as many as 100, analyte-binding domains conjugated to at least one, and preferably more than one, nucleic acid(s).

Proximity-probe based detection assays and particularly proximity extension assays, have proved very useful in the specific and sensitive detection of proteins in a number of different applications, e.g. the detection of weakly expressed or low abundance proteins. However, such assays are not without their problems and room for improvement exists, with respect to both the sensitivity and specificity of the assay.

The sensitivity of the conventional proximity assays, e.g. proximity extension assays, as described above, is limited by two main factors: (i) the affinity of the analyte-binding domains for the target analyte and (ii) the non-specific background signal arising from the random proximity of non-bound probes, particularly probe pairs. Using probes having binding domains with high affinity for the analyte, sensitivity is limited to the detection of approximately 6000 molecules. Traditionally, in order to achieve a low level of background, very low concentrations of proximity probes must be used. This precludes any attempt to compensate for probes comprising low affinity analyte-binding domains by using higher concentrations of probe. It has therefore been found that this may limit the sensitivity of the assay, and the range over which quantitative results may be obtained.

Other methods for reducing non-specific background signal have been proposed, such as using blocking reagents, e.g. blocking oligonucleotides, which bind to the free ends of the nucleic acid domains on the proximity probes until displaced by, e.g. a displacer oligonucleotide. The addition of a displacer oligonucleotide after the proximity probes have been allowed to bind to the analyte means that interaction of the nucleic acid domains of the proximity probes is likely to occur only for the proximity probes bound to the target analyte. Further methods for reducing background signal have centred on improving the detection of the nucleic acid extension product.

However, there is still room to improve the level of background signal and in order to overcome the limitations of the proximity assay, particularly proximity extension assays known in the art, as described above, it has now been found that the use of a component comprising 3' exonuclease activity, before or contemporaneously with the extension reaction, significantly improves the sensitivity and specificity of the assay. Preferably the component comprising 3' exonuclease activity is contacted with the sample at the same time as the component used for the extension of the nucleic acid domains, e.g. a polymerase enzyme. In a particularly preferred embodiment, the polymerase used to extend the nucleic acid domains comprises 3' exonuclease activity.

By including in the assay a component that is capable of degrading non-proximal nucleic acid domains (domains with a free and unprotected 3' end), i.e. degrading nucleic acid domains that have not formed a (stable) sequence specific duplex with a nucleic acid domain of a proximity probe bound to the same target analyte, it is possible to reduce the non-specific background signal present in the assay. Alternatively put, the use of a component comprising 3' exonuclease activity may be seen as reducing or preventing the production of unwanted, undesired or non-specific extension products.

Whilst the use of components comprising 3' exonuclease activity is well known in methods used for producing nucleic acid molecule extension products, the use of said activity in methods for detecting an analyte in a sample, particularly in the proximity extension assays of the present invention provides a unique and unexpected advantage over previous proximity probe based assays.

In general, components of proximity probe based assays are selected specifically to avoid the degradation of other components in the assay. Degrading, destroying or corrupting part or all of the proximity probes, particularly the nucleic acid domains, would be expected to impede or hamper the production of the nucleic acid molecule that acts as the signal to indicate the presence of the target analyte, for example, by reducing the concentration of potential interacting partners.

Furthermore, the presence of such an activity may be seen as an obstacle to the further amplification of the nucleic acid product, i.e. said activity would need to be removed to avoid degradation of the signal nucleic acid molecule or components required for the amplification reaction. The addition of further steps to an analyte detection assay is generally undesirable because it reduces the simplicity of the method thereby increasing the difficulty of automation and/or adaptation to high throughput use. Similarly, the addition of components to the assay increases the complexity of the sample, which may be expected to reduce the sensitivity of the assay.

The method of the present invention, however, relies on the superior reduction in background (i.e. an increase in the signal:noise ratio) seen when a component comprising 3' exonuclease activity is contacted with the sample in a PEA. In particular the 3' exonuclease activity is advantageously supplied as part of the nucleic acid polymerase used to extend the nucleic acid domains of the proximity probes. Alternatively or additionally, the component comprising 3' exonuclease activity may be provided as an independent component (i.e. a separate entity not coupled to, or part of, a polymerase enzyme). Thus it can be seen that the component comprising 3' exonuclease activity can be contacted with the sample in any appropriate form.

Whilst not wishing to be bound by theory, it is theorised that the 3' exonuclease activity is able to degrade the nucleic acid domains of unbound proximity probes with a free and unprotected 3' end (e.g. where the nucleic acid domain is coupled to the analyte-binding domain by its 5' end and where the "free" 3' end is not modified to be resistant to 3' exonuclease activity). In this respect, only duplexes formed between the nucleic acid domains of proximity probes that are both bound to the target analyte may form a stable interaction (under the conditions of the assay, the proximity probes are not easily dissociated from the target analyte once bound, thereby enabling a steady, i.e. non-transient or lasting, duplex to be formed). The formation of a duplex acts to protect the nucleic acid domain of the proximity probe from the 3' exonuclease activity. However, proximity probes that are not bound to the target analyte cannot form a stable duplex, i.e. free/unbound probes (not bound to the target analyte) may interact with the nucleic acid domains of other proximity probes or components in the sample only transiently (forming an unstable and temporary interaction or duplex). Hence, at any one time the unbound probes of the assay are likely to be in a non-hybridised state and those unbound probes comprising a nucleic acid domain with a free and unprotected 3' end will be a substrate for the 3' exonuclease component. The degradation of the nucleic acid domains of these unbound probes prevents the production of non-specific extension products that might otherwise arise in an assay where unbound probes are allowed to persist, e.g. due to extension products arising from duplexes formed by transient or non-specific interactions with nucleic acid domains of proximity probes or other components in the sample.

It is the addition of this 3' exonuclease component that results in an improved reduction in non-specific background signal in a proximity-probe extension assay. As shown in more detail in the Examples, the present invention represents a significant advance over the proximity extension assays known in the art. Surprisingly, it is shown that a reduction in non-specific background activity is observed in the methods of the invention which use a component comprising 3' exonuclease activity, even in samples that comprise already high levels of exonuclease activity, e.g. plasma. The addition of the 3' exonuclease component results in a similar improvement in the signal:noise ratio in assays performed using samples containing target analyte in both buffer and plasma, which was entirely unexpected. The consequence of such a reduction in background signal is an increase in both the specificity and sensitivity of the proximity-probe detection assays.

Moreover, the methods disclosed herein also include a simplified PEA, wherein the components used to amplify the extension product can be combined with the components of the extension assay prior to the inactivation of the component comprising 3' exonuclease. As discussed below, the component comprising 3' exonuclease activity would be expected to degrade certain components of the amplification reaction, e.g. PCR primers, thereby necessitating the addition of these components only after the 3' exonuclease activity has been inactivated. However, the methods disclosed herein describe the modification of various components that enable the reagents of both stages of the assay to be pre-mixed. Advantageously, this results in fewer pipetting steps and less hands-on time, which allows easy automation of the assay and reduction in error.

Accordingly, the invention can be seen to provide the use of a component comprising 3' exonuclease activity in a proximity-probe extension assay to detect an analyte in a sample, wherein the extension product is subsequently amplified and detected.

More particularly, the component comprising 3' exonuclease activity is used during the step of generating an extension product in the proximity-probe extension assay, and put more specifically during the step of conducting a polymerase-catalysed extension reaction to generate an extension product following interaction of the nucleic acid domains of proximity probes used in the proximity assay (such interaction generally being hybridisation of the nucleic acid domains, and subsequent extension of at least one domain; generally speaking the nucleic acid domains hybridise such that one nucleic acid domain may template the extension of another domain). Thus, the component having 3' exonuclease activity is included in the step of generating the initial extension product in the proximity-probe based extension assay, or in other words the step of generating an extension product from interaction of the nucleic acid domains of proximity probes in a proximity probe extension assay.

Alternatively viewed, this aspect of the invention provides a method of detecting an analyte in a sample, which method comprises a proximity-probe extension assay, wherein said assay comprises the use of a component comprising 3' exonuclease activity in the extension step of the assay, and the extension product is subsequently amplified and detected.

Viewed from yet another aspect, the invention provides a method of reducing non-specific extension products (or improving the signal:noise ratio) in a proximity-probe extension assay for detecting an analyte in a sample, said method comprising including in the extension step of said assay a component comprising 3' exonuclease activity, wherein the specific extension product is subsequently amplified and detected.

As noted above, the extension step of a proximity probe extension assay is the step of generating the initial extension product which is subsequently detected as a means of detecting the analyte. In other words, the extension step is the step of generating an extension product based on interaction of the nucleic acid domains of proximity probes, specifically hybridisation of the nucleic acid domains and subsequent extension of at least one of the domains, for example using the other as template.

The method of the invention is, and the component comprising 3' exonuclease activity is for use in, a proximity-probe based assay, and the probe is a proximity probe. The proximity probe based assay may be any of the assays known in the art, for example as described above, which use proximity probes to detect an analyte in a sample. Specifically, the assay is a proximity extension assay, being based on the detection of interactions between the nucleic acid domains of proximity probes by hybridisation, and extension of one or more of those domains.

Accordingly, in one preferred aspect the present invention provides a method for detecting an analyte in a sample, comprising:

(a) contacting said sample with at least one set of at least first and second proximity probes, which probes each comprise an analyte-binding domain and a nucleic acid domain and can simultaneously bind to the analyte;

(b) allowing the nucleic acid domains of the proximity probes to interact with each other upon binding of said proximity probes to said analyte, wherein said interaction comprises the formation of a duplex;

(c) contacting said sample with a component comprising 3' exonuclease activity;

(d) extending the 3' end of at least one nucleic acid domain of said duplex to generate an extension product, wherein the step may occur contemporaneously with or after step (c); and (e) amplifying and detecting the extension product.

As described in more detail below, the analyte-binding domain may bind the analyte directly or indirectly.

It will be seen therefore that the component comprising 3' exonuclease activity may be used to extend the sensitivity and/or specificity of a proximity extension assay. The methods of the invention may thus be considered as methods of increasing the signal:noise ratio of proximity extension assay (for an analyte). Expressed another way, the methods of the present invention may be used to reduce the amount of non-specific extension products in a proximity extension assay. Alternatively, the invention may be viewed as providing a method of disrupting or inhibiting the formation of non-specific duplexes in proximity extension assays. Yet further still, the invention may be seen to provide a method of degrading the nucleic acid domain of unbound proximity probes in proximity extension assays.

As described briefly above, proximity extension assays concern the extension of at least one nucleic acid domain following the formation of a duplex between the nucleic acid domains of two or more proximity probes, when said probes are bound to the target analyte. However, said duplex (the hybridisation of two complementary nucleic acid domains) may be formed in many ways, depending on the orientation of the nucleic acid domain on the proximity probe.

A representative sample of proximity extension assay formats is shown schematically in FIG. 1 and these embodiments are described in detail below. However, these different "versions" of PEA are in no way intended to be limiting on the scope of the invention. Other permutations would be apparent to the skilled person from the below description and are intended to be encompassed by the present invention. In essence, the present invention requires simply that at least one of the proximity probes (which is not limited to a proteinaceous molecule or an antibody, as shown, although this is a preferred aspect of the invention) has a nucleic acid domain comprising a free 3' end that is capable of being extended, and wherein said extension may be templated by the nucleic acid domain of a second proximity probe. In this regard, and as described in more detail below, the nucleic acid domains of the proximity probes may be single-stranded or partially double stranded, but are configured such that single stranded regions of the domains are available for interaction with each other by hybridisation. The nucleic acid domains of respective proximity probes may also interact by each hybridising to a common "splint" nucleic acid molecule, thereby indirectly forming a duplex. Thus in step (b) of the method set out above, the interaction of the nucleic acid domains to form a duplex may be direct or indirect; the nucleic acid domains which are attached to the analyte-binding domains of the proximity probes may hybridise to each other to form a duplex directly or they may form a duplex indirectly by each hybridising to a further nucleic acid molecule. Such a further nucleic acid molecule may be regarded as the second strand of a partially double stranded nucleic acid domain; it will hybridise to at least a region of a nucleic acid molecule attached to the analyte binding domain of a proximity probe (thereby forming a partially double stranded nucleic acid domain which is attached via one strand thereof), leaving a terminal (e.g. 3') single stranded region which is complementary to a region of the nucleic acid domain of another proximity probe, and which is therefore available for interaction by hybridisation with the nucleic acid domain of said other proximity probe. Alternatively the "splint" may be provided as the nucleic acid domain of a further proximity probe.

Version 1 of FIG. 1 depicts a "conventional" proximity extension assay, wherein the nucleic acid domain (shown as an arrow) of each proximity probe is attached to the analyte-binding domain (shown as an inverted "Y") by its 5' end, thereby leaving two free 3' ends. When said proximity probes bind to their respective analyte-binding targets on the analyte (the analyte is not shown in the figure) the nucleic acid domains of the probes, which are complementary at their 3' ends, are able to interact by hybridisation, i.e. form a duplex. The addition of, e.g. a nucleic acid polymerase enzyme, allows each nucleic acid domain to be extended using the nucleic acid domain of the other proximity probe to template that extension. In accordance with the methods of the invention the extension products may be specifically amplified and detected, thereby detecting the target analyte.

Version 2 of FIG. 1 depicts an alternative proximity extension assay, wherein the nucleic acid domain of the first proximity probe is attached to the analyte-binding domain by its 5' end and the nucleic acid domain of the second proximity probe is attached to the analyte-binding domain by its 3' end. The nucleic acid domain of the second proximity probe therefore has a free 5' end (shown as a blunt arrow), which cannot be extended using a typical nucleic acid polymerase enzyme (which extend only 3' ends). The 3' end of the second proximity probe is effectively "blocked", i.e. it is not "free" and it cannot be extended because it is conjugated to, and therefore blocked by, the analyte-binding domain. In this embodiment, when the proximity probes bind to their respective analyte-binding targets on the analyte, the nucleic acid domains of the probes, which share a region of complementary at their 3' ends, are able to interact by hybridisation, i.e. form a duplex. However, in contrast to version 1, only the nucleic acid domain of the first proximity probe (which as a free 3' end) may be extended using the nucleic acid domain of the second proximity probe as a template. As above, the extension product may be amplified and detected, thereby detecting the target analyte.

In version 3 of FIG. 1, like version 2, the nucleic acid domain of the first proximity probe is attached to the analyte-binding domain by its 5' end and the nucleic acid domain of the second proximity probe is attached to the analyte-binding domain by its 3' end. The nucleic acid domain of the second proximity probe therefore has a free 5' end (shown as a blunt arrow), which cannot be extended. However, in this embodiment, the nucleic acid domains which are attached to the analyte binding domains of the respective proximity probes do not have regions of complementarity and therefore are unable to form a duplex directly. Instead, a third nucleic acid molecule is provided that has a region of homology with the nucleic acid domain of each proximity probe, which acts as a "molecular bridge" or a "splint" between the nucleic acid domains. This "splint" oligonucleotide bridges the gap between the nucleic acid domains, allowing them to interact with each other indirectly, i.e. each nucleic acid domain forms a duplex with the splint oligonucleotide. Thus, when the proximity probes bind to their respective analyte-binding targets on the analyte, the nucleic acid domains of the probes each interact by hybridisation, i.e. form a duplex, with the splint oligonucleotide. It can be seen therefore that the third nucleic acid molecule or splint may be regarded as the second strand of a partially double stranded nucleic domain provided on one of the proximity probes. For example, one of the proximity probes may be provided with a partially double-stranded nucleic acid domain, which is attached to the analyte binding domain via the 3' end of one strand and in which the other (non-attached) strand has a free 3' end. Thus such a nucleic acid domain has a terminal single stranded region with a free 3' end. In this embodiment the nucleic acid domain of the first proximity probe (which as a free 3' end) may be extended using the "splint oligonucleotide" (or single stranded 3' terminal region of the other nucleic acid domain) as a template and may advantageously be ligated to the 5' end of the nucleic acid domain (specifically the 5' end of the attached strand, or alternatively put the 5' end of the double-stranded portion of the nucleic acid domain) of the second proximity probe. Alternatively or additionally, the free 3' end of the splint oligonucleotide (i.e. the unattached strand, or the 3' single-stranded region) may be extended using the nucleic acid domain of the first proximity probe as a template. As above, the extension products may be amplified and detected, thereby detecting the target analyte.

As is apparent from the above description, in one embodiment, the splint oligonucleotide may be provided as a separate component of the assay. In other words it may be added separately to the reaction mix (i.e. added separately to the proximity probes to the sample containing the analyte). Notwithstanding this, since it hybridises to a nucleic acid molecule which is part of a proximity probe, and will do so upon contact with such a nucleic acid molecule, it may nonetheless be regarded as a strand of a partially double-stranded nucleic acid domain, albeit that it is added separately. Alternatively, the splint may be pre-hybridised to one of the nucleic acid domains of the proximity probes, i.e. hybridised prior to contacting the proximity probe with the sample. In this embodiment, the splint oligonucleotide can be seen directly as part of the nucleic acid domain of the proximity probe, i.e. wherein the nucleic acid domain is a partially double stranded nucleic acid molecule, e.g. the proximity probe may be made by linking a double stranded nucleic acid molecule to an analyte-binding domain (preferably the nucleic acid domain is conjugated to the analyte-binding domain by a single strand) and modifying said nucleic acid molecule to generate a partially double stranded nucleic acid domain (with a single stranded overhang capable of hybridising to the nucleic acid domain of the other proximity probe). Hence, the extension of the nucleic acid domain of the proximity probes as defined herein encompasses also the extension of the "splint" oligonucleotide. Advantageously, when the extension product arises from extension of the splint oligonucleotide, the resultant extended nucleic acid strand is coupled to the proximity probe pair only by the interaction between the two strands of the nucleic acid molecule (by hybridisation between the two nucleic acid strands). Hence, in these embodiments, the extension product may be dissociated from the proximity probe pair using denaturing conditions, e.g. increasing the temperature, decreasing the salt concentration etc. This is particularly useful in a heterogeneous format, wherein the target analyte is bound to a solid substrate, because the extension products can be separated easily from other components of the assay, e.g. the proximity probes bound to the immobilised analyte may be in the solid phase, whereas the extension product, following denaturation, may be in the liquid phase.

Whilst the splint oligonucleotide depicted in Version 3 of FIG. 1 is shown as being complementary to the full length of the nucleic acid domain of the second proximity probe, this is merely an example and it is sufficient for the splint to be capable of forming a duplex with the ends (or near the ends) of the nucleic acid domains of the proximity probes, i.e. to bridge the gap, as defined further below.

In another embodiment, the splint oligonucleotide may be provided as the nucleic acid domain of a third proximity probe as described in WO 2007/107743, which is incorporated herein by reference, which demonstrates that this can further improve the sensitivity and specificity of proximity probe assays.

Version 4 of FIG. 1, is a modification of Version 1, wherein the nucleic acid domain of the first proximity probe comprises at its 3' end a sequence that is not fully complementary to the nucleic acid domain of the second proximity probe. Thus, when said proximity probes bind to their respective analyte-binding targets on the analyte the nucleic acid domains of the probes are able to interact by hybridisation, i.e. form a duplex, but the extreme 3' end of the nucleic acid domain (the part of the nucleic acid molecule comprising the free 3' hydroxyl group) of the first proximity probe is unable to hybridise and therefore exists as a single stranded, unhybridised, "flap". On the addition of, e.g. a nucleic acid polymerase enzyme, only the nucleic acid domain of the second proximity probe may be extended using the nucleic acid domain of the first proximity probe to template that extension. As discussed above, the extension product may be specifically amplified and detected, thereby detecting the target analyte.

In this embodiment, it may be beneficial to modify one or more nucleotides at the 3' end of the nucleic acid domain of the first proximity probe, e.g. to be resistant to 3' exonuclease activity. Suitable modifications are described further below. If the nucleic acid domain is resistant to 3' exonuclease activity, then only the nucleic acid domain of the second proximity probe may be extended. In contrast, if the nucleic acid domain is susceptible to 3' exonuclease activity, then the "flap" may be degraded resulting in a 3' end that is fully hybridised (annealed) to the nucleic acid domain of the second proximity probe. Hence, the nucleic acid domain of the first proximity probe also may be extended using the nucleic acid domain of the second proximity probe as a template.

The final embodiment depicted in FIG. 1, namely Version 5, could be viewed as a modification of Version 3. However, in contrast to Version 3, the nucleic acid domains of both proximity probes are attached to their respective analyte-binding domains by their 5' ends. In this embodiment the 3' ends of the nucleic acid domains are not complementary and hence the nucleic acid domains of the proximity probes cannot interact or form a duplex directly. Instead, a third nucleic acid molecule is provided that has a region of homology with the nucleic acid domain of each proximity probe which acts as a "molecular bridge" or a "splint" between the nucleic acid domains. This "splint" oligonucleotide bridges the gap between the nucleic acid domains, allowing them to interact with each other indirectly, i.e. each nucleic acid domain forms a duplex with the splint oligonucleotide. Thus, when the proximity probes bind to their respective analyte-binding targets on the analyte, the nucleic acid domains of the probes each interact by hybridisation, i.e. form a duplex, with the splint oligonucleotide. In accordance with Version 3, it can be seen therefore that the third nucleic acid molecule or splint may be regarded as the second strand of a partially double stranded nucleic domain provided on one of the proximity probes. In a preferred example, one of the proximity probes may be provided with a partially double-stranded nucleic acid domain, which is attached to the analyte binding domain via the 5' end of one strand and in which the other (non-attached) strand has a free 3' end. Thus such a nucleic acid domain has a terminal single stranded region with at least one free 3' end. In this embodiment the nucleic acid domain of the second proximity probe (which as a free 3' end) may be extended using the "splint oligonucleotide" as a template. Alternatively or additionally, the free 3' end of the splint oligonucleotide (i.e. the unattached strand, or the 3' single-stranded region of the first proximity probe) may be extended using the nucleic acid domain of the second proximity probe as a template. As above, the extension products may be amplified and detected, thereby detecting the target analyte.

As discussed above on connection with Version 3, the splint oligonucleotide may be provided as a separate component of the assay. On the other hand, since it hybridises to a nucleic acid molecule which is part of a proximity probe, and will do so upon contact with such a nucleic acid molecule, it may be regarded as a strand of a partially double-stranded nucleic acid domain, albeit that it is added separately. Alternatively, the splint may be pre-hybridised to one of the nucleic acid domains of the proximity probes, i.e. hybridised prior to contacting the proximity probe with the sample. In this embodiment, the splint oligonucleotide can be seen directly as part of the nucleic acid domain of the proximity probe, i.e. wherein the nucleic acid domain is a partially double stranded nucleic acid molecule, e.g. the proximity probe may be made by linking a double stranded nucleic acid molecule to an analyte-binding domain (preferably the nucleic acid domain is conjugated to the analyte-binding domain by a single strand) and modifying said nucleic acid molecule to generate a partially double stranded nucleic acid domain (with a single stranded overhang capable of hybridising to the nucleic acid domain of the other proximity probe). Hence, the extension of the nucleic acid domain of the proximity probes as defined herein encompasses also the extension of the "splint" oligonucleotide. Advantageously, when the extension product arises from extension of the splint oligonucleotide, the resultant extended nucleic acid strand is coupled to the proximity probe pair only by the interaction between the two strands of the nucleic acid molecule (by hybridisation between the two nucleic acid strands). Hence, in these embodiments, the extension product may be dissociated from the proximity probe pair using denaturing conditions, e.g. increasing the temperature, decreasing the salt concentration etc. This is particularly useful in a heterogeneous format, wherein the target analyte is bound to a solid substrate, because the extension products can be separated easily from other components of the assay, e.g. the proximity probes bound to the immobilised analyte may be in the solid phase, whereas the extension product, following denaturation, may be in the liquid phase.

Whilst the splint oligonucleotide depicted in Version 5 of FIG. 1 is shown as being complementary to the full length of the nucleic acid domain of the first proximity probe, this is merely an example and it is sufficient for the splint to be capable of forming a duplex with the ends (or near the ends) of the nucleic acid domains of the proximity probes, i.e. to bridge the gap, as defined further below.

In another embodiment, the splint oligonucleotide may be provided as the nucleic acid domain of a third proximity probe as described in WO 2007/107743, which is incorporated herein by reference, which demonstrates that this can further improve the sensitivity and specificity of proximity probe assays.

From the above it will be understood that there are multiple permutations of proximity extension assays, which all rely on the formation of a nucleic acid duplex comprising an extensible 3' end (for templated extension) on the interaction between two (or more) proximity probes, when such probes are bound to the analyte. The interaction between the probes (or more specifically, between their respective nucleic acid domains, which includes splint oligonucleotides) is thus proximity-dependent; the binding of the detection probes, together, on the analyte brings them into proximity, such that they (or more particularly, their nucleic acid domains) may interact. Accordingly, by detecting the interaction (or the extension products generated therefrom), the analyte may be detected. In the method of the invention, the proximity probes may interact by hybridisation to each other (directly or indirectly) to allow the extension of one or more nucleic acid molecules. This extension may result in the nucleic acid domains of two proximity probes being conjugated, or joined to one another, and a splint oligonucleotide (which may form part of the nucleic acid domain of a proximity probe) assists in or mediates this interaction (conjugation). The extension (and if applicable the conjugation) may be detected by detecting the extension and/or conjugation product (interaction product).

Whilst not wishing to be bound by theory, it is believed that the method of the invention relies upon the addition of a component comprising 3' exonuclease activity degrading the free and unprotected 3' ends of nucleic acid domains of unbound proximity probes. It is thought that the nucleic acid domains of said unbound probes would otherwise bind non-specifically and/or transiently (temporarily) to other unbound proximity probes or components of the assay to generate non-specific/background extension products, thereby interfering with the detection of the analyte.

Exonucleases are enzymes that work by cleaving nucleotides one at a time from the end of a polynucleotide chain by hydrolyzing phosphodiester bonds at either the 3' or the 5' end. Thus exonucleases exist as either 5' or 3' exonucleases, which nomenclature refers to the end from which cleavage is initiated, i.e. 3' exonucleases degrade nucleic acid molecules in the 3' to 5' direction. Numerous types of exonuclease enzyme are known to exist, which degrade DNA and/or RNA and may act on double stranded or single stranded nucleic acids. Whilst exonucleases may be distinct entities (separate enzymes with the sole function of degrading nucleic acids), e.g. a 5' RNA exonuclease, which is found in both eukaryotes and prokaryotes for the turnover of mRNA and exonuclease I from *E. coli*, which degrades single stranded DNA in a 3'-5' direction, much exonuclease activity arises from enzymes with multiple functions, e.g. many DNA polymerases comprise also 3' and/or 5' exonuclease activity (DNA polymerase I from *E. coli*).

Hence, a component comprising 3' exonuclease activity for use in the methods of the invention includes any element that is capable of degrading a nucleic acid from its 3' end. In a preferred aspect of the invention, the component comprising 3' exonuclease activity acts preferentially on single stranded nucleic acids, i.e. it has a greater activity on single stranded molecules than double stranded, e.g. at least 2, 3, 4, 5, 10, 20, 50 or 100 times more activity on single stranded nucleic acid molecules.

The component comprising exonuclease activity must be capable of degrading, fully or partially, the nucleic acid domain of unbound proximity probes, i.e. probes not bound to the target analyte, wherein said nucleic acid domains have a free and unprotected 3' end. As discussed below, the nucleic acid domain of the proximity probes may consist of any nucleotide residues that are capable of participating in Watson-Crick type or analogous base pair interactions. However, in embodiments where the nucleic acid domains comprise DNA the component comprising 3' exonuclease activity acts on DNA, and preferably has a higher activity on DNA than RNA e.g. it has at least 2, 3, 4, 5, 10, 20, 50 or 100 times more activity on DNA than RNA. Similarly, in embodiments where the nucleic acid domains comprise RNA the component comprising 3' exonuclease activity acts on RNA, and preferably has a higher activity on RNA than DNA e.g. it has at least 2, 3, 4, 5, 10, 20, 50 or 100 times more activity on RNA than DNA.

In one aspect of the invention, the component comprising 3' exonuclease activity is an enzyme. In a particularly preferred embodiment the enzyme is a nucleic acid polymerase capable of extending the 3' end of nucleic acid molecule that also comprises 3' exonuclease activity. Specifically, the component comprising 3' exonuclease activity may be selected from any one or more of the group comprising T4 DNA polymerase, T7 DNA polymerase, Phi29 (φ29) DNA polymerase, DNA polymerase I, Klenow fragment of DNA polymerase I, *Pyrococcus furiosus* (Pfu) DNA polymerase and/or *Pyrococcus woesei* (Pwo) DNA polymerase. Hence, in some embodiments the component comprising 3' exonuclease activity may be a hyperthermophilic enzyme, particularly a hyperthermophilic polymerase comprising 3' exonuclease activity, such as Pfu DNA polymerase or Pwo DNA polymerase.

Hyperthermophilic enzymes are typically enzymes derived or obtained from hyperthermophilic organisms, namely organisms that grow optimally at extreme temperatures above 90° C., for example at around 100° C. (as compared with optimal growth at around 70° C., which is typical for most thermophiles). A hyperthermophilic polymerase (or more particularly a polymerase from a hyperthermophilic organism) may have optimum enzymatic activity at above normal biological temperatures, e.g. above 37° C., such as above 40, 50, 60 or 70° C., typically above 60° C. or 70° C. Significantly, such an enzyme will advantageously exhibit low, or reduced, activity at lower temperatures such as at room temperature, e.g. at 25° C., or at 30° C. Particularly advantageously, polymerase activity may be low until a temperature of at least 45° C. or 50° C. is reached. Such enzymes have been identified from organisms that live in extreme temperature conditions, e.g. archaea (such as *Pyrococcus furiosus* and *Pyrococcus woesei* etc). Enzymes of particular interest from these organisms are polymerase enzymes, which have been useful in the development of many molecular biology techniques, most notably PCR. As well as naturally occurring hyperthermophilic enzymes, thermostable enzymes with a high temperature optimum may be modified in order to confer the property of reduced or low activity at room temperature, in order to create an enzyme with the same or similar properties, specifically the same or similar temperature activity profile, as a naturally occurring hyperthermophilic enzyme, namely the combination of a high temperature optimum (e.g. above 50, 55, or 60° C.) with low or reduced activity at room temperature (or at a lower temperature such as 30° C., 37° C. or 40° C.). Such modified polymerase enzymes include for example so-called "hot start" derivatives of Taq polymerase, which e.g. gain activity at about 50° C. As used herein, the term "hyperthermophilic polymerase" includes not only naturally occurring enzymes but also all such modified derivatives, including also derivatives of naturally occurring hyperthermophilic polymerase enzymes. Particularly preferred hyperthermophilic enzymes for use in the methods of the present application include Pfu DNA polymerase and Pwo DNA polymerase and derivatives, e.g. sequence-modified derivatives, or mutants thereof. Although in certain embodiments, a hyperthermophilic polymerase may be advantageous or preferred, it is not necessary to use such an enzyme and in other embodiments any thermophilic or thermostable polymerase may be used e.g. Taq polymerase (that it any polymerase enzyme exhibiting stability at high temperatures, or an increased temperature optimum).

In another embodiment, the polymerase activity for extension of the proximity probe nucleic acid domain (and/or splint oligonucleotide) may be provided by an enzyme with no or minimal 3' exonuclease activity, e.g. the α subunit of DNA polymerase III from *E. coli*, the Klenow exo(−) fragment of DNA polymerase I, Taq polymerase, Pfu (exo⁻) DNA polymerase, Pwo (exo⁻) DNA polymerase etc., and the component comprising 3' exonuclease may be provided as a separate entity, e.g. another enzyme comprising 3' exonuclease activity. Hence, the polymerase enzyme with no or minimal 3' exonuclease activity may be a hyperthermophilic or thermostable polymerase. In a further embodiment, the component comprising 3' exonuclease activity may be included in multiple forms, i.e. more than one component comprising 3' exonuclease activity may be provided, e.g. as part of the polymerase enzyme and as an independent enzyme that has as its primary function, 3' exonuclease activity. In one aspect of the invention, the component comprising 3' exonuclease activity is exonuclease I.

Advantageously the component comprising 3' exonuclease activity is contacted with the sample before or contemporaneously with the component required for the extension of the nucleic acid domain, but after the nucleic acid domains of the proximity probes have been allowed to interact, i.e. to form a duplex. In this respect, the nucleic domains of the proximity probes must be at least partially single stranded on contact with the sample such that they can interact with each other on binding to the target analyte. Thus, if the component comprising 3' exonuclease activity was present (present in an active form) prior to the formation of the aforementioned duplex, the nucleic acid domains of all of the proximity probes with a free and unprotected 3' end would be susceptible to degradation. In contrast, once the duplex has been allowed to form between proximity probes bound to the target analyte, then only the nucleic acid domains of unbound proximity probes are available for degradation. As discussed above, probes not bound to the target analyte do not form a stable duplex, and whilst they may interact with other non-bound probes or other components of the sample, these interactions are likely to be transient (temporary), thereby meaning that the nucleic acid domains of these probes will be available substrates for the component comprising 3' exonuclease activity.

Where the component comprising 3' exonuclease activity is contacted with the sample contemporaneously with the component required for the extension of the nucleic acid domain, e.g. wherein the polymerase enzyme comprises 3' exonuclease activity, the extension and degradation reactions will occur simultaneously.

Where the component comprising 3' exonuclease activity is contacted with the sample before the component required for the extension of the nucleic acid domain, e.g. wherein an independent enzyme comprising 3' exonuclease activity (and no substantial or detectable polymerase activity) is contacted with the sample, the nucleic acid domains with free and unprotected 3' ends of unbound probes will be degraded and the component comprising 3' exonuclease activity may be inactivated (e.g. removed, inhibited or denatured) prior to the extension reactions. However, the 3' exonuclease activity may be retained during the extension step.

In one embodiment, the component comprising 3' exonuclease activity is inactivated prior to the step of amplifying the extension product to prevent degradation of components required for the amplification step. The term "inactivated" means that the component is inhibited, denatured, e.g. by heat, or physically removed from the sample. In this respect, only the 3' exonuclease activity need be inactivated.

For example, wherein the extension product is amplified by PCR, standard unmodified primers (with free and unprotected 3' ends) would be a substrate for the 3' exonuclease and failure to inactivate this activity would result in degradation of these PCR reagents and therefore limited or no amplification.

In a preferred embodiment, some or all of the reagents for the amplification reaction are added to the sample before it is contacted with the component comprising 3' exonuclease activity. In a particularly preferred embodiment said reagents are added between steps (b) and (c) as defined above. Alternatively, some or all of the reagents for the amplification reaction are added to the sample at the same time as, i.e. simultaneously or contemporaneously with, the component comprising 3' exonuclease activity.

In one embodiment, the primers are provided in a modified form such that they are resistant to 3' exonuclease activity. Modifications to nucleic acid molecules or to nucleotides contained within a nucleic acid molecule, to prevent degradation by exonucleases are well known in the art and generally utilise the modification of one or more residues at the protected end, e.g. the 3' end. Any modification that is suitable for the protection against 3' exonuclease activity may be utilised in the methods of the invention. In this respect, the primers for use in the present invention preferably comprise at least one modified nucleotide at the 3' end. For instance, the modifications may be selected from any one or more of the list comprising a thiophosphate-modified nucleotide, a locked nucleic acid nucleotide (inaccessible RNA nucleotide), a 2'-OMe-CE Phosphoramidite modified nucleotide, or a peptide nucleic acid nucleotide.

For the step of amplifying the extension product of the method of the invention it is advantageous to use "hot start" primers (described in Kaboev et al., 2000, Nuc. Acids Res., 28(21), pp. e94, which is incorporated herein by reference). Hot start primers are oligonucleotide primers which comprise a stem-loop structure by virtue of complementary regions at the 5' and 3' ends. In this respect, the primer is designed to be complementary to the target sequence (a specific region in the extension product) and at least 5-6 nucleotides are added to the 5' end of the primer that form a sequence that is complementary to the 3' end of the primer. At low temperatures, e.g. the temperature at which the components of the reaction are mixed and/or the extension reaction is performed, the primers form a stem loop structure and cannot serve as an effective primer for amplification of the extension product. However, after heating to the annealing temperature of the PCR, the primers acquire a linear structure and primer extension (amplification) can begin. The use of hot start primers is believed to prevent inference of the PCR primers with the interaction between proximity probes of the method and to further protect said primers from 3' exonuclease activity.

The term "amplifying" or "amplified" is used generally herein to include any means of increasing the number of copies of the extension product, or part thereof, in the assay as a means of signalling the presence of the target analyte in the sample. For instance, any amplification means known in the art may be utilised in the methods of the invention, e.g. PCR, LCR, RCA, MDA etc. Depending on the abundance of the target analyte in the sample, it may be necessary to amplify the extension product, or part thereof, such that the concentration of the extension product has doubled, i.e. 2 times the number of copies present before amplification. Alternatively, it may be preferable to increase the number of copies by multiple orders of magnitude. In some embodiments amplification results in the sample comprising at least 2, 3, 4, 5, 6, 7, 8, 9, 10, 15, 20, 50 or 75 times the original amount of extension product or part thereof. In further preferred embodiments it may be preferable to amplify the extension product such that the sample comprises at least $10^2$, $10^3$, $10^4$, $10^5$, $10^6$, $10^7$, $10^8$, $10^9$, $10^{10}$ etc. times the original amount of extension product or part thereof.

It will be apparent that it is not necessary to amplify all of an extension product in order to determine whether the sample comprises the target analyte. It is necessary to amplify only a portion of the extension product that was not present in the sample before the extension reaction occurred. For example, the extension product will effectively comprise two parts: a first "old" part (the existing part) containing the nucleotide sequence that made up the nucleic acid domain of the proximity probe (or splint) and a second "new" part (the extended part) containing the nucleotide sequence generated by the templated extension reaction. It is the detection of the second "new" or "extended" part that allows the detection of the of the target analyte, i.e. if there is no analyte, there will be no extension and hence no "new" or "extended" part. Thus, in a preferred aspect of the invention, the step of amplifying the extension product comprises amplifying a portion of the extended part of the extension product.

A portion of the extended part need be of sufficient size that it can be distinguished from other sequences present in the sample. In effect, the portion of the extended part of the extension product acts as a unique identifier or signal that corresponds to the presence of the target analyte. Hence, if the portion comprises a nucleotide sequence that is not otherwise present in the sample, the amplification of this sequence is sufficient to signal the presence and quantity of the target analyte in the sample.

Thus, the portion may comprise at least 8 nucleotides, preferably at least 9, 10, 11, 12, 13, 14, 15, 16, 17, 18, 19, 20 nucleotides. Portions of the extended part of the extension product may generally be in the range of between about 8 up to about 1000 nucleotides in length, where in certain embodiments they may range from about 8 to about 500 nucleotides in length including from about 8 to about 250 nucleotides in length, e.g., from about 8 to about 160 nucleotides in length, such as from about 12 to about 150 nucleotides in length, from about 14 to about 130 nucleotides in length, from about 16 to about 110 nucleotides in length, from about 8 to about 90 nucleotides in length, from about 12 to about 80 nucleotides in length, from about 14 to about 75 nucleotides in length, from about 16 to about 70 nucleotides in length, from about 16 to about 60 nucleotides in length, and so on. In certain representative embodiments, the extended part of the extension product may range in length from about 10 to about 80 nucleotides in length, from about 12 to about 75 nucleotides in length, from about 14 to about 70 nucleotides in length, from about 34 to about 60 nucleotides in length, and any length between the stated ranges.

Whilst it is envisaged that the whole of the extension product may be amplified, i.e. both the existing and extended parts, it is sufficient that the amplification product comprises at least a portion of the extended part of the extension product. In one aspect of the invention, primers may be designed to flank either side of the portion of the extended part of the extension product and amplification of that portion, e.g. by PCR, and the amplification product (comprising the portion of the extended product) may be detected as described below. In another aspect of the invention, the portion of the extended part of the extension product may form the template for the ligation of, e.g. a padlock probe (as described elsewhere herein) to form a circular oligonucleotide and amplification of that sequence, e.g. by rolling circle amplification (RCA), would result in an amplification product comprising multiple copies of the sequence corresponding to the portion of extended part of the extension product. Thus, in this way the extension product, or more particularly a part thereof, may be amplified. Alternatively or additionally, the portion of extended part of the extension product may act as a primer for RCA of a circular oligonucleotide comprising a sequence that is complementary to the extended part of the extension product. As above, the resulting product would comprise multiple copies of the sequence corresponding to the portion of extended part of the extension product, which could be detected as described below. Thus in this embodiment also the extension product, or more particularly a part thereof, is amplified.

In embodiments where the "splint" oligonucleotide is extended, said extended oligonucleotide may be circularised to provide a template for amplification, preferably rolling circle amplification. In these embodiments, the 3' end (the extended end) of the extended oligonucleotide is ligated to the 5' end of the extended oligonucleotide (the non-extended end), wherein said ligation can be mediated by any suitable means, as described elsewhere herein. In a particularly preferred embodiment the ligation reaction is a templated ligation, wherein the 3' and 5' ends of the extended oligonucleotide are brought into proximity to each other by hybridisation to a nucleic acid molecule, e.g. an oligonucleotide that is added to the reaction to act as a "splint" or "molecular bridge" between the 3' and 5' ends of the extended oligonucleotide (as defined elsewhere herein). On hybridisation of the ends of the extended oligonucleotide to the "splint" nucleic acid molecule, the ends may be ligated, e.g. by the activity of a ligase enzyme, to form a circular oligonucleotide which contains the extended part of the extension product. Hence, amplification of said circular oligonucleotide, e.g. by rolling circle amplification, results in the amplification of the extension product. In this case, the amplification product comprises a sequence that is the complement of the extended part of the extension product. Hence, amplification of the circularised oligonucleotide results in the indirect amplification of the extension product.

It will be apparent from the above, that the extended part of the extension product need comprise only a relatively small number of nucleotides. Furthermore, the maximum size of the extension product will be dependent on the size of the nucleic acid domains of the proximity probes and/or splint oligonucleotide (as defined below) which act as the template for the extension product. The extension product may result from full or partial extension of the nucleic acid domain and/or splint oligonucleotide, i.e. the extension reaction may result in extension products that have been extended to the end of the template nucleic acid or the extension reaction may be using conditions such that the extension product is only a partial complementary strand of the template nucleic acid.

The term "detecting" or "detected" is used broadly herein to include any means of determining the presence of the analyte (i.e. if it is present or not) or any form of measurement of the analyte. In the method of the invention the analyte is detected indirectly by amplifying the extension product (which includes amplifying a product based on, or derived from, or generated using, the extension product) and detecting said amplification product. Hence, detecting the analyte is equivalent to detecting the amplification product as defined above and these terms are used interchangeably herein.

Thus "detecting" may include determining, measuring, assessing or assaying the presence or absence or amount or location of analyte in any way. Quantitative and qualitative determinations, measurements or assessments are included, including semi-quantitative. Such determinations, measurements or assessments may be relative, for example when two or more different analytes in a sample are being detected, or absolute. As such, the term "quantifying" when used in the context of quantifying a target analyte(s) in a sample can refer to absolute or to relative quantification. Absolute quantification may be accomplished by inclusion of known concentration(s) of one or more control analytes and/or referencing the detected level of the target analyte with known control analytes (e.g., through generation of a standard curve). Alternatively, relative quantification can be accomplished by comparison of detected levels or amounts between two or more different target analytes to provide a relative quantification of each of the two or more different analytes, i.e., relative to each other.

The "analyte" may be any substance (e.g. molecule) or entity it is desired to detect by the method of the invention. The analyte is the "target" of the assay method of the invention. The analyte may accordingly be any biomolecule or chemical compound it may be desired to detect, for example a peptide or protein, or nucleic acid molecule or a small molecule, including organic and inorganic molecules. The analyte may be a cell or a microorganism, including a virus, or a fragment or product thereof. It will be seen therefore that the analyte can be any substance or entity for which a specific binding partner (e.g., an affinity binding partner) can be developed. All that is required is that the analyte is capable of simultaneously binding at least two binding partners (more particularly, the analyte-binding domains of at least two proximity probes). Proximity probe-based assays, such as that of the present invention, have found particular utility in the detection of proteins or polypeptides. Analytes of particular interest may thus include proteinaceous molecules such as peptides, polypeptides, proteins or prions or any molecule which includes a protein or polypeptide component, etc., or fragments thereof. In a particularly preferred embodiment of the invention, the analyte is a wholly or partially proteinaceous molecule. The analyte may be a single molecule or a complex that contains two or more molecular subunits, which may or may not be covalently bound to one another, and which may be the same or different. Thus in addition to cells or microrganisms, such a complex analyte may also be a protein complex. Such a complex may thus be a homo- or hetero-multimer. Aggregates of molecules e.g. proteins may also be target analytes, for example aggregates of the same protein or different proteins. The analyte may also be a complex between proteins or peptides and nucleic acid molecules such as DNA or RNA. Of particular interest may be the interactions between proteins and nucleic acids, e.g. regulatory factors, such as transcription factors, and DNA or RNA.

All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared or they may be prior-treated in any convenient way e.g. for storage.

Representative samples thus include any material which may contain a biomolecule, or any other desired or target analyte, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, blood cells, urine, faeces, cerebrospinal fluid or any other body fluids (e.g. respiratory secretions, saliva, milk, etc), tissues, biopsies, cell cultures, cell suspensions, conditioned media or other samples of cell culture constituents, etc. The sample may be pre-treated in any convenient or desired way to prepare for use in the method of the invention, for example by cell lysis or purification, isolation of the analyte, etc.

The proximity probes for use in the method of the invention comprise an analyte-binding domain and a nucleic acid domain, and are in effect detection probes which bind to the analyte (via the analyte-binding domain), the binding of which may be detected (to detect the analyte) by means of detecting the interaction which occurs between the nucleic acid domains thereof upon such binding. Accordingly the probes may be viewed as nucleic acid-tagged affinity ligands or binding partners for the analyte, the analyte-binding domain being the affinity binding partner, and the nucleic acid domain the nucleic acid tag. The nucleic acid domain is coupled to the analyte-binding domain and this "coupling" or connection may be by any means known in the art, and which may be desired or convenient and may be direct or indirect e.g. via a linking group. For example, the domains may be associated with one another by covalent linkage (e.g. chemical cross-linking) or by non-covalent association e.g., via streptavidin-biotin based coupling (biotin being provided on one domain and streptavidin on the other).

The analyte binding domain may be any binding partner for the target analyte, and it may be a direct or indirect binding partner therefor. Thus it may bind to the target analyte directly, or indirectly via an intermediary molecule or binding partner which binds to the target analyte, the analyte binding domain binding to said intermediary molecule (binding partner). Particularly, the analyte-binding domain or the intermediary binding partner is a specific binding partner for the analyte. A binding partner is any molecule or entity capable of binding to its target, e.g. target analyte, and a specific binding partner is one which is capable of binding specifically to its target (e.g. the target analyte), namely that the binding partner binds to the target (e.g. analyte) with greater affinity and/or specificity than to other components in the sample. Thus binding to the target analyte may be distinguished from non-target analytes; the specific binding partner either does not bind to non-target analytes or does so negligibly or non-detectably or any such non-specific binding, if it occurs, may be distinguished. The binding between the target analyte and its binding partner is typically non-covalent.

The analyte binding domain may be selected to have a high binding affinity for a target analyte. By high binding affinity is meant a binding affinity of at least about $10^{-4}$ M, usually at least about $10^{-6}$ M or higher, e.g., $10^{-9}$ M or higher. The analyte binding domain may be any of a variety of different types of molecules, so long as it exhibits the requisite binding affinity for the target protein when present as part of the proximity probe. In other embodiments, the analyte binding domain may be a ligand that has medium or even low affinity for its target analyte, e.g., less than about $10^{-4}$ M.

The analyte binding domain may be a small molecule or large molecule ligand. By small molecule ligand is meant a ligand ranging in size from about 50 to about 10,000 daltons, usually from about 50 to about 5,000 daltons and more usually from about 100 to about 1000 daltons. By large molecule is meant a ligand ranging in size from about 10,000 daltons or greater in molecular weight.

The small molecule may be any molecule, as well as a binding portion or fragment thereof, that is capable of binding with the requisite affinity to the target analyte. Generally, the small molecule is a small organic molecule that is capable of binding to the target analyte of interest. The small molecule will include one or more functional groups necessary for structural interaction with the target analyte, e.g. groups necessary for hydrophobic, hydrophilic, electrostatic or even covalent interactions. Where the target analyte is a protein, the small molecule ligand will include functional groups necessary for structural interaction with proteins, such as hydrogen bonding, hydrophobic-hydrophobic interactions, electrostatic interactions, etc., and will typically include at least an amine, amide, sulfhydryl, carbonyl, hydroxyl or carboxyl group, preferably at least two of the functional chemical groups. The small molecule may also comprise a region that may be modified and/or participate in covalent linkage to the nucleic acid domain of the proximity probe, without substantially adversely affecting the small molecule's ability to bind to its target analyte.

Small molecule affinity ligands often comprise cyclical carbon or heterocyclic structures and/or aromatic or polyaromatic structures substituted with one or more of the above functional groups. Also of interest as small molecules are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The small molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc, to produce structural analogs.

As such, the small molecule may be obtained from a library of naturally occurring or synthetic molecules, including a library of compounds produced through combinatorial means, i.e. a compound diversity combinatorial library. When obtained from such libraries, the small molecule employed will have demonstrated some desirable affinity for the protein target in a convenient binding affinity assay. Combinatorial libraries, as well as methods for their production and screening, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

The analyte binding domain may also be a large molecule. Of particular interest as large molecule analyte binding domains are antibodies, as well as binding fragments and derivatives or mimetics thereof. Where antibodies are the analyte binding domain, they may be derived from polyclonal compositions, such that a heterogeneous population of antibodies differing by specificity are each "tagged" with the same tag nucleic acid (nucleic acid domain) or monoclonal compositions, in which a homogeneous population of identical antibodies that have the same specificity for the target analyte are each tagged with the same tag nucleic acid. As such, the analyte binding domain may be either a monoclonal or polyclonal antibody. In yet other embodiments, the affinity ligand is an antibody binding fragment or derivative or mimetic thereof, where these fragments, derivatives and mimetics have the requisite binding affinity for the target analyte. For example, antibody fragments, such as Fv, F(ab)$_2$ and Fab may be prepared by cleavage of the intact protein, e.g. by protease or chemical cleavage. Also of interest are recombinantly or synthetically produced antibody fragments or derivatives, such as single chain antibodies or scFvs, or other antibody derivatives such as chimeric antibodies or CDR-grafted antibodies, where such recombinantly or synthetically produced antibody fragments retain the binding characteristics of the above antibodies. Such antibody fragments or derivatives generally include at least the $V_H$ and $V_L$ domains of the subject antibodies, so as to retain the binding characteristics of the subject antibodies. Such antibody fragments, derivatives or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments, derivatives and mimetics thereof may be obtained from commercial sources and/or prepared using any convenient technology, where methods of producing polyclonal antibodies, monoclonal antibodies, fragments, derivatives and mimetics thereof, including recombinant derivatives thereof, are known to those of the skill in the art.

Also suitable for use as binding domains are polynucleic acid aptamers. Polynucleic acid aptamers may be RNA oligonucleotides which may act to selectively bind proteins, much in the same manner as a receptor or antibody (Conrad et al., Methods Enzymol. (1996), 267 (Combinatorial Chemistry), 336-367). In certain embodiments where the analyte binding domain is a nucleic acid, e.g., an aptamer, the target analyte is not a nucleic acid.

Importantly, the analyte binding domain will be one that includes a moiety that can be covalently attached to the nucleic acid domain without substantially abolishing the binding affinity of the analyte binding domain to its target analyte.

In addition to antibody-based peptide/polypeptide or protein-based binding domains, the analyte binding domain may also be a lectin, a soluble cell-surface receptor or derivative thereof, an affibody or any combinatorially derived protein or peptide from phage display or ribosome display or any type of combinatorial peptide or protein library. Combinations of any analyte-binding domain may be used.

The binding sites on the analyte for the respective analyte-binding domains of the proximity probes in a set may be the same or different. Thus, for example in the case of a homomeric protein complex or aggregate comprising two or more identical subunits or protein constituents, the analyte-binding domains of two or more probes may be the same. Where the analyte is a single molecule or comprises different sub-units or constituents (e.g. a heteromeric complex or an aggregate of different proteins), the analyte binding domains will be different.

Since the length of the nucleic acid domain of the proximity probes can be constructed to span varying molecular distances, binding sites on the analyte for the analyte binding domain need not be on the same molecule. They may be on separate, but closely positioned, molecules. For example, the multiple binding domains of an organism, such as a bacteria or cell, or a virus, can be targeted by the methods of the present invention.

As noted above, the analyte-binding domain may bind to the analyte directly or indirectly. In the case of indirect binding, the target analyte may first be bound by a specific binding partner (or affinity ligand), and the analyte-binding domain of the proximity probe may bind to the specific binding partner. This enables the design of proximity probes as universal reagents. For example the analyte-specific binding partner may be an antibody, and a universal proximity probe set may be used to detect different analytes by binding to the Fc regions of the various different analyte-specific antibodies.

The nucleic acid domains of the first and second proximity probes may be regarded as the nucleic acid "tags" which interact to form a detectable product, which may be detected to report the detection of the analyte. The nucleic acid domains may thus be regarded as reactive nucleic acid functionalities which interact to provide the signal by means of which the analyte is detected (more particularly to form a signal-giving product). Put another way, the nucleic acid domains may be regarded as "detection tags", which interact to form, or enable the formation of, a "detectable" tag or product. When two or more analytes are present in the same sample they may be detected simultaneously using two or more sets of proximity probes, each set of proximity probes being designed to form on interaction one or more unique nucleic acid sequence extension products or "detectable tags". These unique "detectable tags" may be detected and quantified contemporaneously with or after amplification, separately using methods well known in the literature including liquid chromatography, electrophoresis, mass spectrometry, DNA sequencing, DNA array technology both bead based and planar, and also multi-colour real-time PCR.

In a preferred embodiment, the detectable tag (i.e. the extension product) is amplified and detected by quantitative PCR (qPCR), which is also known as real-time PCR. In a particularly preferred embodiment, the qPCR uses a dye which intercalates with nucleic acid molecules to provide a detectable signal, preferably a fluorescent signal. Fluorescent intercalating dyes that may find particular use in the present invention are SYBR Greene and EvaGreen™, although the qPCR embodiments of the invention are not limited to these dyes.

In the method of the present invention, one or both of the nucleic acid domains of the first and second proximity probes may be extended, which results in the formation of a new nucleic acid molecule or "extension product" which may be amplified and detected.

In some embodiments the nucleic acid domains may be ligated together, following the extension of one of the nucleic acid domains, to produce the extension products or detectable tags, i.e. the gap between the nucleic acid domains is "filled in" by a polymerase enzyme using the "splint" oligonucleotide as a template. In embodiments where the nucleic acid domains are ligated, this ligation is mediated by a splint, which as discussed above, may be considered to be part of the nucleic acid domain of one of the proximity probes, i.e. wherein the nucleic acid domain is partially double stranded. The splint may be provided separately, either as a free nucleic acid molecule or it can be provided as the nucleic acid domain of a third proximity probe.

The ligation results in the formation of a new nucleic acid molecule or sequence, which may be amplified and detected.

The nucleic acid domains may be a single stranded nucleic acid molecule (e.g. an oligonucleotide), a partially double stranded and partially single stranded molecule, or a double stranded molecule that includes a region that is double stranded and a region where the two nucleic acid strands are not complementary and therefore single stranded. As such, in certain embodiments, the nucleic acid domain is made up of a single stranded nucleic acid. In other embodiments, the nucleic acid domain may be made up of two partially complementary nucleic acid strands, where the two strands include a hybridized region and non-hybridized region.

The nucleic acid domains of the first and second proximity probes must be capable of interaction by hybridisation, i.e. the formation of one or more duplexes. This interaction may be direct, e.g. the nucleic acid domains comprise regions of complementarity to each other, preferably at their 3' ends (although the region of complementarity may be internal to one nucleic acid domain, see e.g. Versions 2 and 4 of FIG. 1), or indirect, e.g. the nucleic acid domains of said first and second proximity probes may each hybridise with a region of a so-called "splint" oligonucleotide.

The nucleic acid domains are generally of a length sufficient to allow interaction with the nucleic acid domain of another proximity probe when bound to a target analyte (or splint-mediated interaction). Nucleic acid domains are usually in the range of between about 8 up to about 1000 nucleotides in length, where in certain embodiments they may range from about 8 to about 500 nucleotides in length including from about 8 to about 250 nucleotides in length, e.g., from about 8 to about 160 nucleotides in length, such as from about 12 to about 150 nucleotides in length, from about 14 to about 130 nucleotides in length, from about 16 to about 110 nucleotides in length, from about 8 to about 90 nucleotides in length, from about 12 to about 80 nucleotides in length, from about 14 to about 75 nucleotides in length, from about 16 to about 70 nucleotides in length, from about 16 to about 60 nucleotides in length, and so on. In certain representative embodiments, the nucleic acid domain may range in length from about 10 to about 80 nucleotides in length, from about 12 to about 75 nucleotides in length, from about 14 to about 70 nucleotides in length, from about 34 to about 60 nucleotides in length, and any length between the stated ranges. In some embodiments, the nucleic acid domains are usually not more than about 28, 29, 30, 31, 32, 33, 34, 35, 36, 37, 38, 39, 40, 41, 42, 44, 46, 50, 55, 60, 65, or 70 nucleotides in length.

The nucleic acid domain may be made up of ribonucleotides and/or deoxyribonucleotides as well as synthetic nucleotide residues that are capable of participating in Watson-Crick type or analogous base pair interactions, i.e. "hybridisation" or the formation of a "duplex". Thus, the nucleic acid domain may be DNA or RNA or any modification thereof e.g. PNA or other derivatives containing non-nucleotide backbones.

The sequence of the nucleic acid domain of the first and second proximity probes (i.e. the "detection" nucleic acid domains) may be any sequences which are capable of forming a duplex and may be chosen or selected with respect to each other or the splint, if present. Thus, the sequence is not critical as long as the first and second domains may hybridise to each other or a third nucleic acid domain (splint). However, the sequences should be chosen to avoid the occurrence of hybridization events other than between the nucleic acid domains of the first and second proximity probes or with that of the splint oligonucleotide. Once the sequence is selected or identified, the nucleic acid domains may be synthesized using any convenient method.

The two components of the proximity probe are joined together either directly through a bond or indirectly through a linking group. Where linking groups are employed, such groups may be chosen to provide for covalent attachment of the nucleic acid and analyte-binding domains through the linking group, as well as maintain the desired binding affinity of the analyte-binding domain for its target analyte. Linking groups of interest may vary widely depending on the analyte-binding domain. The linking group, when present, is in many embodiments biologically inert. A variety of linking groups are known to those of skill in the art and find use in the subject proximity probes. In representative embodiments, the linking group is generally at least about 50 daltons, usually at least about 100 daltons and may be as large as 1000 daltons or larger, for example up to 1000000 daltons if the linking group contains a spacer, but generally will not exceed about 500 daltons and usually will not exceed about 300 daltons. Generally, such linkers will comprise a spacer group terminated at either end with a reactive functionality capable of covalently bonding to the nucleic acid or analyte binding moieties. Spacer groups of interest may include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject proximity probes include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

The proximity probes employed in the subject methods may be prepared using any convenient method. In representative embodiments, nucleic acid domains may be conjugated to the analyte-binding domain, either directly or through a linking group. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used in covalently bonding the components together to produce the proximity probe include: hydroxy, sulfhydryl, amino, and the like. The particular portion of the different components that are modified to provide for covalent linkage may be chosen so as not to substantially adversely interfere with that component's desired binding affinity for the target analyte. Where necessary and/or desired, certain moieties on the components may be protected using blocking groups, as is known in the art, see e.g. Green & Wuts, Protective Groups in Organic Synthesis (John Wiley & Sons) (1991). Methods for producing nucleic acid/antibody conjugates are well known to those of skill in the art. See e.g. U.S. Pat. No. 5,733,523, the disclosure of which is herein incorporated by reference.

In other embodiments, proximity probes may be produced using in vitro protocols that yield nucleic acid-protein conjugates, i.e. molecules having nucleic acids, e.g. coding sequences, covalently bonded to a protein, i.e. where the analyte-binding domain is produced in vitro from vectors which encode the proximity probe. Examples of such in vitro protocols of interest include: RepA based protocols (see e.g., Fitzgerald, Drug Discov. Today (2000) 5:253-258 and WO 98/37186), ribosome display based protocols (see e.g., Hanes et al., Proc. Natl. Acad. Sci. USA (1997) 94:4937-42; Roberts, Curr Opin Chem Biol (1999) June; 3: 268-73; Schaffitzel et al., J Immunol Methods (1999) December 10; 231: 119-35; and WO 98/54312), etc.

In embodiments which utilise a splint oligonucleotide (which may be a nucleic acid domain of a third proximity probe), said splint oligonucleotide functions to mediate the interaction between the nucleic acid domains of the first and second proximity probes (i.e. the "detection" domains). As noted above, the splint oligonucleotide may also act as a nucleic acid domain to be extended, resulting in an extension product to be amplified and detected in accordance with the method of the invention. Thus, the splint may accordingly be viewed a "connector" oligonucleotide which acts to connect or "hold together" the detection domains of the first and second proximity probes, such they may interact, or may be ligated together. Alternatively or additionally, the splint may be viewed as the extendible domain of a nucleic acid domain or tag or a separate nucleic acid domain which acts as a "primer" for extension to generate the extension product for amplification and detection.

In these embodiments the splint hybridises with the nucleic acid domains of the first and second proximity probes. More particularly, the splint hybridises (anneals) simultaneously with the nucleic acid domains of at least the first and second proximity probes. However, wherein the "splint" oligonucleotide is prehybridised to the nucleic acid domain of at least one of said proximity probes, it will be hybridised with the nucleic acid domain of one proximity probe before it hybridises with the other. Nevertheless, the "splint" will preferably hybridise with the nucleic acid domains of both proximity probes at the same time to enable the formation of a stable complex capable of being extended.

When the splint oligonucleotide is provided as the nucleic acid domain of a third proximity probe, this hybridisation of the nucleic acid domains of all of the set of proximity probes to each other increases the avidity of the probe-target complex upon binding to the target analyte. This avidity effect contributes to the sensitivity of the assay by supporting the formation of signal-giving proximity probe-target analyte complexes.

The term "hybridisation" or "hybridises" as used herein refers to the formation of a duplex between nucleotide sequences which are sufficiently complementary to form duplexes via Watson-Crick base pairing. Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary A=U or U=A base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule or the domains that are determined to be complementary. The nucleic acid domains of the first and second proximity probes thus contain a region of complementarity for the nucleic acid domain the other proximity probe. Alternatively, where a splint oligonucleotide is used, the first and second proximity probes contain a region of complementarity for the splint oligonucleotide (which may be present on a third proximity probe), and conversely the splint oligonucleotide contains regions of complementarity for each of the nucleic acid domains of the first and second proximity probes.

The regions of complementarity (i.e. hybridisation regions) may have a length in the range of 4-30 bp e.g. 6-20, 6-18, 7-15 or 8-12 bp.

The splint nucleic acid domain is generally of a length sufficient to provide for the above described simultaneous binding of nucleic acid domains of the first and second probes. In representative embodiments, the splint oligonucleotides range in length from about 6 to about 500 nucleotides, including from about 20 to about 40 nucleotides, e.g. from about 25 to about 30 nucleotides.

As noted above, the interaction between the nucleic acid domains of the first and second proximity probes is primarily the formation of a duplex, wherein one or both of the nucleic acid domains may be extended, particularly template-directed extension using the nucleic acid domain of the other proximity probe as the template. This may result in the formation of a completely double stranded nucleic acid, e.g. where both domains are extended fully, or a partially double stranded molecule, e.g. where only one strand is extended or both strands are extended partially. Thus extension of one or both of the nucleic acid domains may be considered to be a "joining" of the respective domains, e.g. the production of one double stranded nucleic acid from two single stranded molecules.

In other embodiments, this "joining" may be a ligation, particularly wherein, e.g. the nucleic acid domain of the first proximity probe is extended such that its 3' end is in proximity with the 5' end of the second proximity probe to allow the template-directed ligation of the two domains. In such a case, it will clearly be understood that the ligation template will be provided by the splint, which may form part of one of the nucleic acid domains or may be provided separately free in solution or as a nucleic acid domain of a third proximity probe. Such a ligation may be carried out using a ligase enzyme, which may, e.g. be added to the reaction after the polymerase mediated extension of the nucleic acid domain of the first proximity probe.

Thus, in a preferred embodiment of the method of the invention, the nucleic acid domains of the first and second probes are ligatable by means of a reaction templated by the hybridised splint, said nucleic acid domains are ligated (following extension of one of the nucleic acid domains) and the "ligation" product, which is also an extension product, is amplified and detected. In such an embodiment, the splint may therefore be viewed as a "splint template" or "ligation template" or "template oligonucleotide". In such embodiments, the splint may also be extended to produce a further "extension product", which amplified and detected.

As discussed above, for the various interactions between the nucleic acid domains to take place, the nucleic acid domains of the first and second proximity probes need to be coupled to the analyte-binding domains in certain orientations. For example, for the extension of both domains wherein said domains comprise single stranded nucleic acids, each nucleic acid domain must be coupled to the analyte-binding domain by its 5' end, leaving a free 3' hydroxyl end, which may "anneal" or "hybridise" when in proximity. However, for the extension of a single domain and/or the conjugation of the two domains, it is typical (although not essential, see Version 4 of FIG. 1) to couple the nucleic acid domain of a first proximity probe by its 5' end (leave a free 3' hydroxyl end, which may be extended) while the other domain will be coupled via its 3' end (leaving a free 5' phosphate end, which cannot be extended using a convention polymerase).

In embodiments wherein the nucleic acid domains are ligatable, the respective first and second nucleic acid domains hybridise to the splint or wherein the nucleic acid domain of one of the proximity probes is partially double stranded with a singled stranded overhang, the nucleic acid domain of the other proximity probe hybridises with a domain of the overhang. The domain with the 3' end may then be extended by template directed extension up to the 5' phosphate of the other domain, wherein a ligase enzyme may be utilised to join the two strands together. Thus, the respective 3' and 5' ends are not be hybridised immediately adjacent to one another on the splint (template) but hybridise to the splint leaving a space (or a stretch of nucleotides) between them.

The gap or space or stretch of nucleotides between the two ends is in the range of between about 8 up to about 1000 nucleotides in length, where in certain embodiments they may range from about 8 to about 500 nucleotides in length including from about 8 to about 250 nucleotides in length, e.g., from about 8 to about 160 nucleotides in length, such as from about 12 to about 150 nucleotides in length, from about 14 to about 130 nucleotides in length, from about 16 to about 110 nucleotides in length, from about 8 to about 90 nucleotides in length, from about 12 to about 80 nucleotides in length, from about 14 to about 75 nucleotides in length, from about 16 to about 70 nucleotides in length, from about 16 to about 60 nucleotides in length, and so on. In certain representative embodiments, the nucleic acid domain may range in length from about 10 to about 80 nucleotides in length, from about 12 to about 75 nucleotides in length, from about 14 to about 70 nucleotides in length, from about 34 to about 60 nucleotides in length, and any length between the stated ranges. In some embodiments, the nucleic acid domains are usually not more than about 28, 29, 30, 31, 32, 33, 34, 35, 36, 37, 38, 39, 40, 41, 42, 44, 46, 50, 55, 60, 65, or 70 nucleotides in length.

Thus, the splint may include a first 3' region of complementarity for the nucleic acid domain of the 5' free proximity probe and a second 5' region of complementarity for the nucleic acid domain of the 3' free proximity probe. The first and second regions of the splint may be 3 to 20, 6 to 17, 6 to 15 or 6 to 12 or 8 to 12 nucleotides in length, e.g. about 13 to 17, 12 to 16, 11 to 15, or 12 to 14 nucleotides in length or about 6 to 12, 7 to 11 or 8 to 10 nucleotides in length.

As will be described in more detail below, amplification of the ligation/extension product is performed before or contemporaneously with the detection process. Accordingly, it may in some embodiments be desirable to design the splint so as to minimise any false amplification which may take place in such a step, for example any possibility of the splint acting as a template for the polymerase used in the amplification. Thus for example the splint may be provided as an RNA oligonucleotide or a DNA/RNA hybrid; Taq polymerase typically used in amplification reactions cannot use an RNA template. Alternatively, a similar effect may be achieved using a DNA splint with two short hybridisation regions; since the hybridisation is weak, such a splint will not template DNA polymerisation at the high temperatures used in PCR.

Alternatively, in other preferred embodiments the splint is advantageously extended to produce an extension product as defined above, which will itself be amplified and detected in accordance with the methods of the invention.

In certain embodiments a sample may be assayed for two or more different target analytes. In such embodiments, the sample is contacted with a set of proximity probes for each target analyte, such that the number of sets contacted with the sample may be two or more, e.g., three or more, four or more etc. Such methods find particular use in multiplex and high-throughput applications.

The amount of proximity probes that is added to a sample may be selected to provide a sufficiently low concentration of proximity probe in the reaction mixture to ensure that the proximity probes will not randomly come into close proximity with one another in the absence of binding to a target analyte, at least not to any great or substantial degree. As such, it is intended that only when the proximity probes bind the analyte through the binding interaction between the analyte-binding domains of the proximity probes and the binding sites of the analyte, do the proximity probes come into close proximity to one another.

However, it has been surprisingly found that the addition of a component comprising 3' exonuclease activity may reduce the number of interactions between proximity probes that are not bound to the target analyte, by degrading nucleic acid domains with a free and unprotected 3' end. In this respect, such interactions are less stable than those between probes bound to the target analyte and are therefore transient. Consequently, said unbound probes are subject to degradation by the component comprising 3' exonuclease activity. Thus, in the methods of the present invention it may be possible to use concentrations of proximity probes that could not be used previously in proximity based detection assays. This is particularly advantageous where the analyte-binding domains of the proximity probes have medium or low affinity for the target analyte and are therefore required at higher concentrations.

In representative embodiments, the concentration of the proximity probes in the reaction mixture following combination with the sample ranges from about 1 fM to 1 µM, such as from about 1 pM to about 1 nM, including from about 1 pM to about 100 nM.

Following combination of the sample and set(s) of proximity probes, the reaction mixture may be incubated for a period of time sufficient for the proximity probes to bind target analyte, if present, in the sample. In representative embodiments, the product mixture may be incubated for a period of time ranging from about 5 minutes to about 48 hours, including from about 30 minutes to about 12 hours, at a temperature ranging from about 4 to about 50° C., including from about 20 to about 37° C. Conditions under which the reaction mixture is maintained should be optimized to promote specific binding of the proximity probe to the analyte, while suppressing unspecific interaction. Conditions should also allow for efficient and specific hybridization between the nucleic acid domains as described above.

In some embodiments, the proximity probes are lyophilized. In one aspect of the invention, said lyophilized proximity probes are rehydrated prior to contact with the sample containing the analyte. In a preferred aspect of the invention, the lyophilized proximity probes are rehydrated upon addition of the sample comprising the target analyte.

In certain embodiments, the effective volume of the incubation mixture is reduced, at least during the portion of the incubation step in which the proximity probes are binding to target analyte, if present in the sample. In these embodiments, the effective volume of the incubation mixture may be reduced for a number of different reasons. In certain embodiments, the effective volume of the incubation mixture is reduced in order to allow for the use of medium and low affinity analyte-binding domains and/or increase the sensitivity of the assay. For example, in certain embodiments where the effective volume of the incubation mixture is reduced, the analyte-binding domains may be medium or low affinity binders, by which is meant that the analyte-binding domains may have a binding affinity for their target analyte that is less than about $10^{-4}$ M, such as about 1 nM Kd. In certain embodiments, the sensitivity of the assay may be increased such that the assay can detect as few as about 100 or fewer target analytes in a 1 µl sample, including as few as about 75 or fewer target analytes in a 1 µl sample, including as few as about 50 or fewer target analytes in a 1 µl sample.

In certain embodiments, a "crowding agent" or "volume excluder" is included in the mixture during the incubation step reviewed above, e.g., to reduce the effective volume of the incubation mixture during binding of the proximity probes to their target analyte. Typically, the "crowding agent" is a water soluble macromolecular material. Suitable macromolecular materials broadly comprise biocompatible natural or synthetic polymers having an average molecular weight of from about 1500 to several million, which do not specifically interact with the other reagents in the mixture, or the product. Such polymers are known in the art as "volume-excluders", as their primary function is to occupy volume in the in vitro reaction medium and provide a highly concentrated environment for biochemical reactions, e.g., approximating in vivo conditions. The volume-excluding polymers must of course be sufficiently soluble to provide the required concentration. Suitable exemplary polymers include, but are not limited to: commercially available polyethylene glycol (PEG) polymers, e.g., having an average molecular weight greater than about 2000, FICOLL polymers such as those having an average molecular weight of about 70,000, bovine plasma albumin, glycogen, polyvinylpyrrolidone, dextran, e.g. Sephadex® which is cross-linked dextran, etc. PEG polymers of higher molecular weights, especially, PEG 1450, PEG 3350, PEG 6000 (also sold as PEG 8000), and PEG 20,000, having average molecular weights of about 1450, 3000-3700, 6000-7500, and 15,000-20,000, respectively, are employed in representative embodiments. PEG 6000 and PEG 8000 are employed in representative embodiments. The concentration of the volume-excluding polymers in the incubation reaction in representative embodiments falls within a range of about 5% w/v to about 45% w/v, depending upon the type of polymer and its molecular weight. In general, it is expected that a given type of polymer of higher molecular weight need be present in lower concentration than the same type of polymer of lower molecular weight to achieve the same effect on enzyme activity.

In a preferred embodiment, the crowding agent or volume excluder is sephadex. In a particularly preferred embodiment, the sephadex is type G-100.

In those embodiments where a volume excluder is employed, prior to the next step of the method, the incubation mixture may be diluted to account for the presence of the volume excluder, e.g., by at least about 2-fold or more, such as at least about 5-fold or more, including at least about 10-fold or more, depending on the amount of volume excluder that is present, the nature of the dilution fluid, etc., where in representative embodiments the dilution fluid is water or some other suitable aqueous fluid of water and one or more solutes, e.g., salts, buffering agents, etc.

Instead of, or in addition to, the use of a volume excluder, the incubation mixture may be reduced in volume during incubation by removing a portion of the water from the incubation mixture, e.g., via evaporation. In these embodiments, the volume of the fluid may be reduced by at least about 2-fold or more, such as at least about 5-fold or more, including at least about 10-fold or more, as desired. Importantly, not all of the water is removed from the incubation mixture in these embodiments. Any convenient protocol may be employed for reducing the volume of the incubation mixture by removing a select portion of the water therefrom. An instrument for controlling evaporation rate by monitoring and adjusting humidity and temperature may be employed, where in certain embodiments the volume of the incubation mixture is monitored, e.g., by continuously measuring the volume of the incubation mixture, where when appropriately evaporated, the polymerase and PCR-mixes may be added, as described above. As desired, a heating block could be used to enhance the evaporation. Alternatively, the volume of the incubation mixture may be reduced by filtrating out water. In representative embodiments, a size exclusion filter is used to selectively contain molecules of sizes larger than a cut off limit while smaller molecules and water is removed by passage through the filter. The force placed on the solution to move it through the filter may be by either centrifugation or vacuum suction.

Upon binding of the binding domains of the proximity probes to the analyte, the nucleic acid domains of the proximity probes come into close proximity to one another. As a result, the nucleic acid domains of the first and second probes are able to hybridise to each other directly or indirectly, e.g. via a splint.

The splint, where present, may be added to the sample before, at the same time as, or after the proximity probes. In one embodiment the splint is pre-hybridised to the proximity probe. In another embodiment, the splint oligonucleotide forms part of the nucleic acid domain of the proximity probe. In yet a further embodiment, the splint oligonucleotide may be coupled to an analyte-binding domain in the form of a third proximity probe, wherein it is preferably added at the same time as the first and second proximity probes.

Following the combination of the sample with the proximity probes, the sample may be diluted, preferably by the addition of the non-enzymatic components of the extension reaction, e.g. buffers, salts, nucleotides etc, but not the component comprising 3' exonuclease activity. In a preferred embodiment, the dilution also comprises the reagents for the amplification reaction, e.g. buffers, salts, nucleotides, primers and polymerase. The dilution step acts to reduce the possibility of interactions between the unbound proximity probes and/or their interaction with other components in the sample.

Dilution may also disrupt the interaction between the nucleic acid domains of the bound probes. However, as the bound probes are in close proximity any interactions that are disrupted will stabilise (i.e. re-anneal or re-hybridise) under the appropriate conditions. Thus in one embodiment the sample may be incubated for a further period of time sufficient for the interaction between the bound proximity probes to stabilise. In representative embodiments, the product mixture may be incubated for a period of time ranging from about 5 minutes to about 48 hours, including from about 30 minutes to about 12 hours, at a temperature ranging from about 4 to about 50° C., including from about 20 to about 37° C. Conditions under which the reaction mixture is incubated should be optimized to maintain specific binding of the proximity probe to the analyte, while suppressing unspecific interaction. Conditions should also allow for efficient and specific hybridization between the nucleic acid domains as described above.

Where the amplification reagents are added to the sample following the step of incubating the probes with the sample it is preferred that the primers are protected from 3' exonuclease activity, e.g. by modification of their 3' ends as described above. In a further preferred embodiment the primers may alternatively or additionally be hot start PCR primers, e.g. stem loop primers. In a preferred embodiment, the polymerase is a thermostable polymerase as defined further below. In yet another preferred embodiment, the buffer and/or salts allow the activity of all enzymes to be added to the sample.

Further to any dilution steps, the component comprising 3' exonuclease activity is then contacted with the sample. This step may include further dilution of the sample, e.g. addition of the component with appropriate buffers and/or other salts/components. As described above, the component comprising 3' exonuclease activity may be added before or contemporaneously with the polymerase enzyme required for the extension reaction. In a preferred embodiment, the polymerase enzyme comprises also 3' exonuclease activity. The sample may be further incubated under the appropriate conditions to allow the 3' exonuclease activity to act on the nucleic acid domains of unbound proximity probes. The conditions should also be conducive to the extension of the nucleic acid domains, if the polymerase is present in the sample. In some embodiments the polymerase may be added after the component comprising 3' exonuclease activity, wherein the sample may be further incubated to allow the extension products to be generated. Incubation conditions will depend on the components used in the reaction and some representative conditions are described above. However, in embodiments in which the polymerase used to extend the nucleic acid domains is a hyperthermophilic polymerase as defined above, e.g. a modified Taq polymerase, Pfu DNA polymerase, Pwo DNA polymerase etc, or a thermostable polymerase such as Taq polymerase, other reaction conditions may be preferred in the exonuclease and/or extension phases of the method, particularly temperature conditions. For instance, the temperature for the extension reaction and, if the polymerase also has 3' exonuclease activity, the exonuclease reaction, may range from about 4 to about 80° C., including from about 20 to about 75° C., from about 30 to about 60° C., or from about 45 to about 55° C. Thus, in some embodiments the temperature for the extension reaction and, if the polymerase also has 3' exonuclease activity, the exonuclease reaction, may be at least 20, 25, 30, 35, 40, 45, 50, 55, 60, 65, 60 or 75° C.

Following the generation of extension products the component comprising 3' exonuclease activity may be inactivated. In a preferred embodiment the 3' exonuclease activity is inactivated by heat denaturation, e.g. 65-80° C. for 10 minutes, although it will be apparent that the required conditions will vary depending on the nature of the component, e.g. hyperthermophilic polymerases comprising 3' exonucleases may not be inactivated by the above conditions. In some embodiments, the heat inactivation may be the first step of the amplification reaction.

Where the amplification reactants were not added to the sample following the step of contacting the proximity probes with the sample, said reactants should be contacted with the sample at this stage. In a preferred embodiment, an aliquot of the sample may be transferred to a new vessel comprising the amplification components, for amplification and detection. In this respect, following the inactivation of the component comprising 3' exonuclease activity, the primers need not be resistant to 3' exonuclease activity.

In some embodiments, the polymerase capable of extending the nucleic acid domains of the proximity probes may also be useful in the amplification reaction, e.g. if the polymerase is a hyperthermophilic or thermostable polymerase as described above, e.g. Pfu DNA polyermase, Pwo DNA polymerase etc.

Where the amplification reagents were added to the sample following the step of contacting the proximity probes with the sample, it is possible to proceed directly with the amplification reaction. In a preferred embodiment, an aliquot of the reaction mixture is transferred to a new vessel for amplification and detection.

In general, any convenient protocol that is capable of detecting the presence of proximity dependent interactions may be employed. The detection protocol may or may not require a separation step.

In one representative embodiment (other representative embodiments of the methods of the invention are described above), the extension product(s) generated from the interaction of the first and second proximity probes is achieved by nucleic acid extension of the free 3' hydroxyl ends of the nucleic acid domains of the first and second proximity probes, and this interaction is detected by subsequent amplification and detection of the extension product. In this representative embodiment, extension of the nucleic acid domains of the first and second proximity probes is achieved by contacting the reaction mixture with a nucleic acid extending activity, e.g. provided by a suitable nucleic acid polymerase, and maintaining the mixture under conditions sufficient for extension of the nucleic acid domains to occur.

As is known in the art, polymerases catalyze the formation of a phosphodiester bond between juxtaposed nucleotides, wherein the nucleotide comprising the 3' hydroxyl moiety (3' end) may form part of an existing polymer of nucleotides, i.e. a nucleic acid. Typically, the nucleic acid is annealed or hybridized to a complementary nucleic acid molecule which acts to template (i.e. a template nucleic acid) the extension of the nucleic acid with the free 3' end. A free nucleotide with a free 5' phosphate moiety that is complementary to the next nucleotide on the template nucleic acid is then joined to the nucleic acid with the free 3' end to extend it and this process is repeated, e.g. until the end of the template is reached. Any convenient polymerase may be employed, where representative polymerases of interest include, but are not limited to, polymerases comprising also a component with 3' exonuclease activity, e.g. T4 DNA polymerase, T7 DNA polymerase, Phi29 ($\phi$29) DNA polymerase, DNA polymerase I, Klenow fragment of DNA polymerase I, Pfu DNA polymerase and/or Pwo DNA polymerase. Polymerases with 3' exonuclease activity may be obtained from any suitable organisms, including but not limited to, prokaryotic, eukaryotic, or archael organisms. Certain RNA polymerases may also be employed in the methods of the invention.

Where the extension step is performed (the extension product is generated) by a polymerase without 3' exonuclease activity, e.g. Klenow exo(−), Taq polymerase, Pfu (exo⁻) DNA polymerase, Pwo (exo⁻) DNA polymerase etc, a component comprising 3' exonuclease, e.g. an exonuclease enzyme, is added to the sample before, or contemporaneously with, the polymerase. Any convenient 3' exonuclease may be employed, e.g. exonuclease I. Certain RNA exonucleases may also be employed in the methods of the invention.

In this extension step, a suitable polymerase and, if required additional 3' exonuclease, and any reagents that are necessary and/or desirable are combined with the reaction mixture and maintained under conditions sufficient for extension of the hybridized nucleic acid domains to occur. Said conditions should also be sufficient for degradation of the nucleic acid domains of unbound proximity probes to occur. Polymerase and exonuclease reaction conditions are well known to those of skill in the art. During extension and/or degradation, the reaction mixture in certain embodiments may be maintained at a temperature ranging from about 4° C. to about 80° C., such as from about 20 to about 75° C., from about 30 to about 60° C., e.g. from about 45 to about 55° C. or from about 20° C. to about 37° C. (depending on the optimum conditions for the polymerase used in the assay) for a period of time ranging from about 5 seconds to about 16 hours, such as from about 1 minute to about 1 hour. In yet other embodiments, the reaction mixture may be maintained at a temperature ranging from about 35° C. to about 45° C., such as from about 37° C. to about 42° C., e.g., at or about 38° C., 39° C., 40° C. or 41° C., or ranging from about 35° C. to about 75° C., such as from above 40° C. to about 60° C. such as from about 45° C. to about 55° C., e.g., at or about 46° C., 47° C., 48° C., 49° C., 50° C., 51° C., 52° C., 53° C., or 54° C., for a period of time ranging from about 5 seconds to about 16 hours, such as from about 1 minute to about 1 hour, including from about 2 minutes to about 8 hours. In a representative embodiment wherein the amplification components are not included before addition of the component comprising 3' exonuclease activity, the extension and degradation reaction mixture includes 70 mM Tris pH7.5, 17 mM ammonium sulfate, 1 mM DTT, 40 µM of each dNTP, 3 mM $MgCl_2$, 62.5 units/ml DNA polymerase, e.g. T4 DNA polymerase. In a representative embodiment wherein the amplification components are included before addition of the component comprising 3' exonuclease activity, the extension and degradation reaction mixture includes 50 mM KCl, 20 mM Tris HCl pH8.4, 0.2 mM of each dNTP, 3 mM $MgCl_2$, SYBR Green I, 20 nM fluorscein, 3'-thioate protected hairpin primers, 25 units/ml iTaq DNA polymerase, and 62.5 units/ml DNA polymerase, e.g. T4 DNA polymerase.

Following extension, the extension products (e.g. extended nucleic acid domains of the first and second probes) are amplified and detected as an indication of the presence, or as a measure of the amount and optionally the location, of analyte in the sample. As described above, the extended product may comprise a single stranded or double stranded nucleic acid molecule. A single stranded nucleic acid molecule may result from the extension of the splint oligonucleotide which may be dissociated from the nucleic acids of the first and second proximity probes or the product of the conjugation of the two proximal nucleic acid domains of the first and second probes terminating at each end in an analyte binding domain.

The next step of the method following the extension step is to determine the presence of the extended product in the reaction mixture in order to detect the target analyte in the sample. In other words, the reaction mixture is screened etc. (i.e., assayed, assessed, evaluated, tested, etc.) for the presence of any resultant extension products in order to detect the presence of the target analyte in the sample being assayed. According to the present invention the detection step involves an amplification step to generate an amplification product which is detected, typically amplification of all or a portion of the extension product.

The extension product, or more particularly the amplification product, produced by the above-described methods may, in the broadest sense, be detected using any convenient protocol. The particular detection protocol may vary depending on the sensitivity desired and the application in which the method is being practiced. In the method of the invention as described herein, the detection protocol may include an amplification component, in which the copy number of the extension product nucleic acid (or part thereof) is increased, e.g., to enhance sensitivity of the particular assay. However, it is possible that in other methods the extension product may be directly detected without any amplification.

Although not a preferred embodiment of the method of the invention, where detection without amplification is practicable, the nucleic acid extension product may be detected in a number of different ways. For example, one or more of the extension product may be directly labelled, e.g., fluorescently, or otherwise spectrophotometrically, or radioisotopically labelled or with any signal-giving label, such that the extension product is directly labelled. In these embodiments, the directly labelled extension product may be size separated from the remainder of the reaction mixture, including unextended oligonucleotides (i.e. nucleic acid domain oligonucleotides or splint oligonucleotides), in order to detect the extended nucleic acid. Alternatively, conformationally selective probes, e.g., molecular beacons (as described in greater detail below) may be employed to detect to the presence of the extension product, where these probes are directed to a sequence that is only present in the extended nucleic acid product.

As indicated above, in a preferred embodiment of the subject methods, the detection step includes an amplification step, where the copy number of extended nucleic acid or part thereof is increased, e.g., in order to enhance sensitivity of the assay. The amplification may be linear or exponential, as desired, where representative amplification protocols of interest include, but are not limited to: polymerase chain reaction (PCR); isothermal amplification, Rolling circle amplification, etc. In a particularly preferred embodiment of the invention, the amplification protocol is quantitative-PCR (qPCR) or real-time PCR.

Rolling circle amplification using padlock probes, e.g. as described in U.S. Pat. No. 6,558,928, or indeed any circular nucleic acid molecule as a template can also be useful in amplifying an existing "signal" nucleic acid molecule or part thereof, e.g. an extension product generated from a proximity extension assay. Thus, in a preferred aspect of method, the extension product (or part thereof) may be amplified by rolling circle amplification. In one embodiment, RCA is performed using padlock probes. In another embodiment, RCA is performed using circular templates (circular oligonucleotides).

Where the detection step includes an amplification step (more specifically a step of in vitro amplification of the extension product or part thereof), the amplified product (or amplification product) may be detected, to detect the analyte.

The polymerase chain reaction (PCR) is well known in the art, being described in U.S. Pat. Nos. 4,683,202; 4,683,195; 4,800,159; 4,965,188 and 5,512,462, the disclosures of which are herein incorporated by reference. In representative PCR amplification reactions, the reaction mixture that includes the above extended nucleic acids or extension product (which may also be viewed as a template nucleic acid in an amplification reaction) is combined with one or more primers that are employed in the primer extension reaction, e.g., the PCR primers (such as forward and reverse primers employed in geometric (or exponential) amplification or a single primer employed in a linear amplification). The oligonucleotide primers with which the template nucleic acid (hereinafter referred to as template DNA for convenience) is contacted will be of sufficient length to provide for hybridization to complementary template DNA under annealing conditions (described in greater detail below). The primers will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers (forward and reverse primers), depending on whether primer extension, linear or exponential amplification of the template DNA is desired.

As discussed above, the primers may be added to the sample before the addition of the component comprising 3' exonuclease activity, wherein said primers have been modified to be resistant to 3' exonuclease activity, e.g. modification of the 3' end. Furthermore, the primers may also be hot start primers, as described above.

In addition to the above components, the reaction mixture produced in the subject methods typically includes a polymerase and deoxyribonucleoside triphosphates (dNTPs). The desired polymerase activity may be provided by one or more distinct polymerase enzymes. In many embodiments, the reaction mixture includes at least a Family A polymerase, where representative Family A polymerases of interest include, but are not limited to: *Thermus aquaticus* polymerases, including the naturally occurring polymerase (Taq) and derivatives and homologues thereof, such as Klentaq (as described in Barnes et al, Proc. Natl. Acad. Sci. USA (1994) 91:2216-2220) or iTaq (BioRad); *Thermus thermophilus* polymerases, including the naturally occurring polymerase (Tth) and derivatives and homologues thereof, and the like. In certain embodiments where the amplification reaction that is carried out is a high fidelity reaction, the reaction mixture may further include a polymerase enzyme having 3'-5' exonuclease activity, e.g., as may be provided by a Family B polymerase, where Family B polymerases of interest include, but are not limited to: *Thermococcus litoralis* DNA polymerase (Vent) as described in Perler et al., Proc. Natl. Acad. Sci. USA (1992) 89:5577-5581; *Pyrococcus* species GB-D (Deep Vent); *Pyrococcus furiosus* DNA polymerase (Pfu) as described in Lundberg et al., Gene (1991) 108:1-6, *Pyrococcus woesei* (Pwo) and the like. Where the reaction mixture includes both a Family A and Family B polymerase, the Family A polymerase may be present in the reaction mixture in an amount greater than the Family B polymerase, where the difference in activity will usually be at least 10-fold, and more usually at least about 100-fold. Usually the reaction mixture will include four different types of dNTPs corresponding to the four naturally occurring bases present, i.e. dATP, dTTP, dCTP and dGTP. In the subject methods, each dNTP will typically be present in an amount ranging from about 10 to 5000 μM, usually from about 20 to 1000 μM.

The reaction mixture prepared in this detection step of the subject methods may further include an aqueous buffer medium that includes a source of monovalent ions, a source of divalent cations and a buffering agent. Any convenient source of monovalent ions, such as KCl, K-acetate, NH$_4$-acetate, K-glutamate, NH$_4$Cl, ammonium sulphate, and the like may be employed. The divalent cation may be magnesium, manganese, zinc and the like, where the cation will typically be magnesium. Any convenient source of magnesium cation may be employed, including MgCl$_2$, Mg-acetate, and the like. The amount of Mg$^{2+}$ present in the buffer may range from 0.5 to 10 mM, but will preferably range from about 3 to 6 mM, and will ideally be at about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

In preparing the reaction mixture of this step of the subject methods, the various constituent components may be combined in any convenient order. For example, the buffer may be combined with primer, polymerase and then template DNA, or all of the various constituent components may be combined at the same time to produce the reaction mixture. In a particularly preferred embodiment, the amplification reactants are combined with the components for the extension and degradation reactions. In this respect, the components of the reaction are preferably suitable for the activity all of the enzymatic components of the reaction, i.e. the component comprising 3' exonuclease activity, the "first" polymerase for the production of the extension products and optionally the "second" polymerase for the amplification step, which may be different to the "first" polymerase. In some embodiments, the "first" and "second" polymerase are the same, i.e. the polymerase is capable of extending the nucleic acid domain(s) of the proximity probe and amplifying at least a portion of the extended domain(s). In further embodiments, the polymerase comprises 3' exonuclease activity. For instance, Phi29 (φ29) DNA polymerase may be useful in embodiments where the product of the extension reaction is detected by RCA, i.e. Phi29 (φ29) DNA polymerase could be used as the 3' exonuclease component, the extension component and the amplification component. A further non-limiting example is Pfu DNA polymerase, which may be useful in embodiments where the product of the extension reaction is detected by PCR, i.e. Pfu DNA polymerase could be used as the 3' exonuclease component, the extension component and the amplification component.

The amplified products of the amplification reaction may be detected using any convenient protocol, where the particular protocol employed may detect the amplification products non-specifically or specifically, as described in greater detail below. Representative non-specific detection protocols of interest include protocols that employ signal producing systems that selectively detect double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR Green, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg. A further intercalating dye that may be of use in the methods of the invention is EvaGreen™ from Biotium Inc.

In a particularly preferred embodiment of the invention the extension product is amplified by PCR, wherein the PCR is quantitative PCR and the amplified nucleic acid molecules are quantified using an intercalating dye. In a preferred embodiment the intercalating dye is selected from SYBR Greene and EvaGreen™.

In yet other embodiments, a signal producing system that is specific for the amplification product, as opposed to double stranded molecules in general, may be employed to detect the amplification. In these embodiments, the signal producing system may include a probe nucleic acid that specifically binds to a sequence found in the amplification product, where the probe nucleic acid may be labelled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probe nucleic acids include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the specifically labelled probe nucleic acids are labelled with "energy transfer" labels. As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. As used herein, "energy transfer pair" refers to any two molecules that participate in energy transfer. Typically, one of the molecules acts as a fluorescent group, and the other acts as a fluorescence-modifying group. "Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another. As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly. As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others' electronic structure. If the fluorescence-modifying group is a quenching group, this will result in the quenching group preventing the fluorescent group from even emitting light.

The energy transfer labelled probe nucleic acid, e.g., oligonucleotide, may be structured in a variety of different ways, so long as it includes a donor, acceptor and target nucleic acid binding domains. As such, the energy transfer labelled oligonucleotides employed in these embodiments of the method are nucleic acid detectors that include a fluorophore domain where the fluorescent energy donor, i.e., donor, is positioned and an acceptor domain where the fluorescent energy acceptor, i.e., acceptor, is positioned. As mentioned above, the donor domain includes the donor fluorophore. The donor fluorophore may be positioned anywhere in the nucleic acid detector, but is typically present at the 5' terminus of the detector. The acceptor domain includes the fluorescence energy acceptor. The acceptor may be positioned anywhere in the acceptor domain, but is typically present at the 3' terminus of the nucleic acid detector or probe.

In addition to the fluorophore and acceptor domains, the energy transfer labelled probe oligonucleotides also include a target nucleic acid binding domain, which binds to a target nucleic acid sequence found in the amplification product of interest (as described above), e.g., under stringent hybridization conditions (as defined above). This target binding domain typically ranges in length from about 10 to about 60 nucleotides, usually from about 15 to about 30 nt. Depending on the nature of the oligonucleotide and the assay itself, the target binding domain may hybridize to a region of the template nucleic acid or a region of the primer extension product. For example, where the assay is a 5' nuclease assay, e.g., in which a TaqMan® type oligonucleotide probe is employed, the target binding domain hybridizes under stringent conditions to a target binding site of the template nucleic acid, which is downstream or 3' of the primer binding site. In alternative embodiments, e.g., in molecular beacon type assays, the target binding domain hybridizes to a domain of a primer extension product. The overall length of the energy transfer labelled oligonucleotides employed in these embodiments, which includes all three domains mentioned above, typically ranges from about 10 to about 60 nucleotides, usually from about 15 to about 30 nucleotides.

In certain embodiments, the energy transfer labelled oligonucleotide is structured such that energy transfer occurs between the fluorophore and acceptor of the energy transfer labelled oligonucleotide probe upon fluorophore excitation when the energy transfer labelled oligonucleotide is not hybridized to target nucleic acid.

In certain embodiments, the oligonucleotide is a single stranded molecule that does not form intramolecular structures and in which energy transfer occurs because the spacing of the donor and acceptor provides for energy transfer in the single stranded linear format. In these embodiments, energy transfer also occurs between the fluorophore and acceptor of labelled oligonucleotide probe upon fluorophore excitation when the labelled oligonucleotide probe is hybridized to a target nucleic acid. Specific examples of such labelled oligonucleotide probes include the TaqMan® type probes, as described in U.S. Pat. No. 6,248,526, the disclosure of which is herein incorporated by reference (as well as Held et al., Genome Res. (1996) 6:986-994; Holland et al., Proc. Natl. Acad. Sci. USA (1991) 88:7276-7280; and Lee et al., Nuc. Acids Res. (1993) 21:3761-3766). In many of these embodiments, the target nucleic acid binding domain is one that hybridizes to, i.e., is complementary to, a sequence of the template nucleic acid, i.e., the target nucleic acid of the target nucleic acid binding domain is a sequence present in the template nucleic acid (i.e., the pseudotarget or surrogate nucleic acid).

In other embodiments, the probe oligonucleotides are structured such that energy transfer does not occur between the fluorophore and acceptor of the energy transfer labelled oligonucleotide probe upon fluorophore excitation when the energy transfer labelled oligonucleotide probe is hybridized to a target nucleic acid. Examples of these types of probe structures include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in provisional application Ser. No. 60/138,376, the disclosure of which is herein incorporated by reference). In many of these embodiments, the target binding sequence or domain comprises a hybridization domain complementary to a sequence of the primer extension product of the amplification reaction, and not to a sequence found in the pseudotarget nucleic acid.

The next step in the subject methods is signal detection from the labelled amplification products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the target nucleic acid via detection of the pseudotarget nucleic acid and/or amplification products thereof. Depending on the particular label employed, detection of a signal may indicate the presence or absence of the target nucleic acid.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter. Fluorescence is suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time.

Where the detection protocol is a real time protocol, e.g., as employed in real time PCR reaction protocols, data may be collected in this way at frequent intervals, for example once every 3 minutes, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles. In a preferred embodiment of the invention, the fluorescence signal is achieved using a dye that intercalates in double stranded nucleic acid molecules, preferably wherein the intercalating dye is selected from SYBR Greene and EvaGreen™.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other. The differential of signal intensities and/or ratios will allow changes in labelled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase or decrease in fluorescence from the sample in the course of or at the end of the amplification reaction is indicative of an increase in the amount of the target analyte present in the sample, e.g., as correlated to the amount of amplification product detected in the reaction mixture, suggestive of the fact that the amplification reaction has proceeded and therefore the target analyte was in fact present in the initial sample. Quantification is also possible by monitoring the amplification reaction throughout the amplification process. Quantification may also include assaying for one or more nucleic acid controls in the reaction mixture, as described above.

In this manner, a reaction mixture may readily be screened (or assessed or assayed etc.) for the presence of target analyte(s). The methods are suitable for detection of a single target analyte as well as multiplex analyses, in which two or more different target analytes are assayed in the sample. In these latter multiplex situations, the number of different sets of probes that may be employed typically ranges from about 2 to about 20 or higher, e.g., as up to 100 or higher, 1000 or higher, etc.

The analysis of many analytes simultaneously and in a single reaction using several different proximity probe sets (multiplexing) is made possible by the increased specificity and sensitivity obtained with the 3' exonuclease method. Each probe set can be designed to produce a unique extension product that can be used to determine the presence or absence, quantity and/or location of the analytes being interrogated by the probe set. The extension product may be detected directly or preferably after amplification using any of the well established methods for analysis of nucleic acid molecules known from the literature including liquid chromatography, electrophoresis, mass spectrometry, microscopy, real-time PCR (quantitative PCR), fluorescent probes etc. A preferred embodiment of the method of the invention utilises quantitative or real-time PCR. Of particular interest is the combination of the present method with a "DNA array" read-out format. Several unique extension products from a multiplexed proximity extension assay as described herein may be hybridized to a standardized DNA array carrying a number of oligonucleotide sequences (tags) complementary to the extension product sequences. Each extension product hybridized to the array may be identified by its location on the DNA array and the detected intensity in a given hybridization spot will be indicative of the quantity of that specific extension product and hence also of the analyte giving rise to that extension product. Detection of the extension products may be accomplished by spectrometry, fluorescence, radioisotopes etc. Fluorescent moieties may conveniently be introduced into the extension products using fluorescently labelled primers or fluorescently labelled nucleotides in the amplification reaction (PCR). The DNA array may be a simple dot-blot array on a membrane containing a small number of spots or a high density array carrying hundreds of thousands of spots.

The method of the invention may be modified in order to further reduce the background associated with non-specific nucleic acid hybridization events. Such modifications include adjustments to the method that will reduce any non-specific nucleic acid hybridization events. In some embodiments, a protein may be added to the mixture containing the sample and the proximity probes in order to reduce weak and non-specific DNA hybridization events. For example, E. coli single strand DNA binding protein has been used to increase the yield and specificity of primer extension reactions and PCR reactions. (U.S. Pat. Nos. 5,449,603 and 5,534,407.) The gene 32 protein (single strand DNA binding protein) of phage T4 apparently improves the ability to amplify larger DNA fragments (Schwartz, et al., Nucl. Acids Res. 18: 1079 (1990)) and enhances DNA polymerase fidelity (Huang, DNA Cell. Biol. 15: 589-594 (1996)). When employed, such a protein will be used to achieve a concentration in the reaction mixture that ranges from about 0.01 ng/µL to about 1 µg/µL; such as from about 0.1 ng/µL to about 100 ng/µL; including from about 1 ng/µL to about 10 ng/µL.

In some embodiments, the background may be reduced by the addition of poly-A RNA and/or bulk RNA in the assay. Bulk RNA is also known as total RNA, i.e. bulk RNA is simply the total RNA extracted from a sample, e.g. a cell, comprising more than one form and preferably all of the different forms of RNA present in said sample, e.g. mRNA, rRNA, microRNA etc.

In other embodiments, partially double stranded nucleic acid may be used as the nucleic acid domain of the first and second proximity probes in order to reduce weak and non-specific DNA hybridization events.

As explained above, the method of the invention is designed such that interaction between the nucleic acid domains of the first and second probes should occur only if the probes are bound to the analyte, because the nucleic acid domains of unbound probes with a free and unprotected 3' ends will be degraded fully or partially by the component comprising 3' exonuclease activity. However, as is the case with all assays of this type, this cannot always be guaranteed and there may be some background interaction of the nucleic acid domains, if the probes come into proximity randomly in solution (the possibility of this is reduced in embodiments that require the nucleic acid domains of the probes to hybridise to one another by means of the splint, in order for such interaction to occur; the chances of all three domains coming into proximity randomly are reduced, compared to two-probe assays, nonetheless this may still under some circumstances occur). To reduce or minimise the possibility of background due to unbound (i.e. unreacted) probes, blocking oligonucleotides may be used in addition to any other blocking reagents described above and known in the art. In a preferred embodiment the sample may be incubated with one or more blocking reagents, e.g. BSA and the like, prior to the addition of the proximity probes.

The blocking oligonucleotides bind (i.e. hybridise or anneal) to the free ends of the nucleic acid domains of the first and second proximity probes. Thus a blocking oligonucleotide may bind to the free 3' OH end of the nucleic acid domain of a 5' proximity probe and to the free 5' phosphate end of the nucleic acid domain of a 3' proximity probe. The binding of the blocking oligonucleotide may be out-competed in the presence of a high local concentration of, e.g. a splint oligonucleotide, such as occurs in some embodiments of the invention. In this way the blocking oligonucleotide may prevent the first and second domains from hybridising to the splint in the absence of analyte binding. In other embodiments, one or more specific "competitor" oligonucleotides may be added to the assay, e.g. after the proximity probes have become associated with the target analyte, to dissociate the blocking oligonucleotide from the ends of the nucleic acid domains of the probes and thereby allowing the domains of probes in proximity to interact. Thus the free ends of the 5' and/or 3' probes may be prevented from interaction until after they have bound to the analyte. In embodiments where a splint oligonucleotide is used and forms a nucleic acid domain of a third proximity probe, when all three probes are bound to the analyte, the local concentration of the splint is sufficient to out-compete the blocking oligonucleotides; the first and second domains hybridise to the splint and the blocking oligonucleotides are replaced. The blocking oligonucleotides thus allow a competition-based strategy to be used to reduce background and thus increase sensitivity of the assay.

The blocking oligonucleotides may range in length from about 4-100 nucleotides, e.g. 6-75 or 10-50. They may hybridise to a region at or near the free end of the nucleic acid domain of the first or second probe ("near" meaning within 1-20 or 1-10, e.g. 1-6 nucleotides of the free 3' or 5' end). The region of hybridisation may be 3-15 nucleotides long e.g. 3-12, 3-10, 3-8, 4-8, 3-6, 4-6.

The blocking oligonucleotides are typically used in an excess over the respective probes, e.g. an excess of 2-1000 fold, e.g. 20-500, 50-300, 100-500, or 100-300 fold e.g., 20, 200 or 300 fold.

The competitor oligonucleotides are typically used in an excess over the blocking oligonucleotide, e.g. an excess of 2-1000 fold, e.g. 20-500, 50-300, 100-500, or 100-300 fold e.g., 20, 200 or 300 fold.

In the case of detecting an analyte with proximity-probes of low affinity and slow binding kinetics, a preincubation step with the proximity-probes at a sufficiently high concentration promotes binding of the proximity probes to the analyte. This preincubation step may be quickly diluted in a large volume of cold buffer (e.g., buffer that does not include the analyte or the proximity probes), and a portion of this dilution subsequently added to a extension reaction mixture. The low temperature, e.g., ranging from about 0° C. to about 20° C., including from about 4° C. to about 10° C., minimizes the dissociation of existing proximity-probe-analyte complexes while the vast dilution results in a decrease of the concentration of the unbound proximity-probes, thereby lowering their reactivity and minimizing the background signal.

In such embodiments, the assay is performed by using a small incubation volume of from about 1 μl to about 20 μl, such as about 1 μl, or about 2 μl, or about 3 μl, or about 4 μl, or about 5 μl or about 6 μl, of sample and proximity probes. The effective concentration of the proximity probes in the final incubation volume is thus diluted, reducing the background while maintaining the signal since the binding between the probes and analyte does not have time to dissociate before the first and the second nucleic acid domains are extended. This approach enables extremely high sensitivity as long as the extension products can be concentrated from the larger volumes, such as over 100 μl or more, and then detecting the proximity dependent interaction. In such embodiments, the probe-probe interactions can be reduced by using single strand binding proteins.

Problems associated with complex samples may be addressed by diluting the complex sample prior to the analysis. This will greatly decrease the amount of proteins the probes may bind unspecifically to thereby lowering concentration of probes required. While the analyte will also be diluted, the high sensitivity of the proximity probing will provide good detection and quantification.

The method of the present invention may be employed homogeneously (i.e. in solution) as described above, or alternatively heterogeneously, using a solid phase, for example, in which bound analyte becomes immobilised on a solid phase, permitting the use of washing steps. The use of solid phase assays offers advantages, particularly for the detection of difficult samples: washing steps can assist in the removal of inhibiting components, and analytes can be enriched from an undesirably large sample volume. Higher concentrations and greater amounts of proximity probes can be used, as unbound analytes and probes can be removed by washing. The ability to remove unbound or unconjugated probes by washing also means that the solid phase assay tolerates lower purity proximity probes by comparison with the homogeneous assay.

Immobilisation of the analyte on a solid phase may be achieved in various ways. Accordingly, several embodiments of the solid phase assay of the invention are contemplated. In one such embodiment, one (or more) of the first or second (or third proximity probes, if used) may be (or may be capable of being) immobilised on a solid phase (or solid support). The analyte can firstly be captured by the one (or more) immobilised (or immobilisable) probes and secondly be bound by subsequently added probe(s). In such a scheme, the previously-mentioned avidity effect may not be present during the binding step but is relevant for the washing steps. Preferably, the analyte is contacted with the solid phase-bound (i.e. immobilised, or immobilisable) probe(s) at the same time as the non-immobilised/non-immobilisable probe(s) are added to the reaction mixture, such that the avidity effect contributes also to the detection (binding) step.

The immobilised proximity probe may be immobilised, i.e. bound to the support, in any convenient way. Thus the manner or means of immobilisation and the solid support may be selected, according to choice, from any number of immobilisation means and solid supports as are widely known in the art and described in the literature. Thus, the probe may be directly bound to the support, for example via the analyte-binding domain (e.g. chemically crosslinked), it may be bound indirectly by means of a linker group, or by an intermediary binding group(s) (e.g. by means of a biotin-streptavidin interaction). Thus, a proximity probe may be provided with means for immobilisation (e.g. an affinity binding partner, e.g. biotin or a hapten, capable of binding to its binding partner, i.e. a cognate binding partner, e.g. streptavidin or an antibody) provided on the support. The probe may be immobilised before or after binding to the analyte. Further, such an "immobilisable" probe may be contacted with the sample together with the support.

The solid support may be any of the well known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc.

The support may be made of glass, silica, latex or a polymeric material. Suitable are materials presenting a high surface area for binding of the analyte. Such supports may have an irregular surface and may be for example porous or particulate e.g. particles, fibres, webs, sinters or sieves. Particulate materials e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 μm, and have a maximum diameter of preferably not more than 10, and e.g. not more than 6 μm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, e.g. the support may be para-magnetic, and thus is displaceable under the action of that field. In other words, a support comprising magnetic particles may readily be removed by magnetic aggregation, which provides a quick, simple and efficient way of separating the particles following the analyte binding steps.

In another embodiment, an immobilised (or immobilisable) analyte-specific probe comprising only a binding domain (i.e. an analyte capture probe) can be used in addition to the non-immobilised proximity probes of the homogeneous assay. Thus in such an embodiment the analyte is first captured by the immobilised or immobilisable capture probe which serves only to immobilise the analyte on the solid phase, and subsequently the immobilised analyte is incubated with the proximity probes. In such an embodiment, the capture probe may be any binding partner capable of binding the analyte, directly or indirectly (e.g. as discussed above in relation to the analyte-binding domain of the proximity probe). More particularly, such a capture probe binds specifically to the analyte. Since this embodiment of the method requires the simultaneous binding of at least three probes (binding domains) to the analyte or analyte complex, potentially at least three different epitopes can be interrogated, conferring high specificity on the assay.

In a further embodiment, the analyte itself may be immobilised (or immobilisable) on the solid phase e.g. by nonspecific absorption. In a particular such embodiment, the analyte may be present within cells, being optionally fixed and/or permeabilised, which are (capable of being) attached to a solid support.

The above-described methods result in detection of splint-mediated proximity dependent interactions that are present in the reaction mixture, which in turn provides a measure of the amount of target analyte in the sample being assayed. The measure may be qualitative or quantitative Accordingly, the above described methods of detecting the presence of one or more target analytes in a complex sample finds use in a variety of different applications.

The subject methods may be used to screen a sample for the presence or absence of one or more target analytes in a sample. As indicated above, the invention provides methods of detecting the presence or quantifying the amount of one or more target analytes in a sample.

The subject methods can be employed to detect the presence of one or more target analytes in a variety of different types of samples, including complex samples having large amounts of non-target entities, where the subject methods provide for detection of the target analytes(s) with high sensitivity. As such, the subject methods are highly sensitive methods of detecting one or more target analytes in a simple or complex sample. The sample that is assayed in the subject methods is, in many embodiments, from a physiological source, as discussed in more detail above.

In addition to detecting a wide variety of analytes, the subject methods may also be used to screen for compounds that modulate the interaction between the analyte binding domain of the proximity probe with the binding region of the analyte i.e. the binding of the analyte-binding domain to the analyte. The term modulating includes both decreasing (e.g., inhibiting) and enhancing the interaction between the two molecules. The screening method may be an in vitro or in vivo format, where both formats are readily developed by those of skill in the art.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays find use in the a variety of methods, including methods of modulating the activity of the target analyte, and conditions related to the presence and/or activity thereof.

Also provided are kits that find use in practicing the subject methods, as described above. For example, in some embodiments, kits for practicing the subject methods include at least one set of proximity probes, which proximity probes each include an analyte binding domain and a nucleic acid domain as described above. As indicated above, the certain protocols will employ two or more different sets of such probes for simultaneous detection of two or more target analytes in a sample, e.g., in multiplex and/or high throughput formats. As such, in certain embodiments the kits will include two or more distinct sets of proximity probes. Furthermore, additional reagents that are required or desired in the protocol to be practiced with the kit components may be present, which additional reagents include, but are not limited to: a component comprising 3' exonuclease activity, one or more polymerase enzymes, splint oligonucleotide (optionally in the form of a third proximity probe), blocking oligonucleotides, competitor oligonucleotides, solid support for immobilisation of probe, binding domain or analyte, means for immobilisation of probe, binding domain or analyte, amplification and detection means e.g. fluorescently labelled nucleotides or oligonucleotides or intercalating dyes (e.g. SYBR Greene and/or EvaGreen™), pairs of supplementary nucleic acids, single strand binding proteins, and PCR amplification reagents (e.g., nucleotides, buffers, cations, etc.), and the like. In certain embodiments, the kits may include elements employed in reducing the effective volume of an incubation mixture, as reviewed above, e.g., a volume excluder. The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, flash drive, etc., on which the information has been recorded. Yet another means that may be present is a website address which may be used via the internet to access the information at a removed site. Any convenient means may be present in the kits.

Accordingly, in a further aspect the present invention provides a kit for use in a method for detecting an analyte in a sample, said kit comprising:

(a) at least one set of at least first and second proximity probes, which probes each comprise an analyte-binding domain and a nucleic acid domain and can simultaneously bind to the analyte; and (b) a component comprising 3' exonuclease activity; and (c) optionally, means for extending the nucleic acid domain of at least one of said first and second proximity probes to generate an extension product; and (d) optionally, means for amplifying and detecting said extension product.

As indicated above, the means for extending the nucleic acid domains may be a polymerase enzyme, and such means may optionally further comprise the reagents necessary for the polymerase reaction (e.g. nucleotides etc). The means for amplifying and detecting the extension product, may be any of the means discussed above in the context of the assay methods e.g. amplification means and means for detecting amplification products thereof e.g. reagents for a PCR reaction (e.g. amplification primers, and optionally polymerase and/or nucleotides, etc.) and for detecting PCR amplicons etc (e.g. Taqmane probes, intercalating dyes, such as SYBR Greene and/or EvaGreen™, etc.).

The kit may further optionally comprise a splint oligonucleotide and/or blocking oligonucleotides for the first and second probes.

The kit may further optionally comprise an immobilised capture probe for the analyte, or a capture probe provided with means for immobilisation. Alternatively, the kit may comprise a solid phase for capture of, or binding to, the analyte, or one or more said first or second proximity probes may be immobilised or provided with means for immobilisation.

The invention will be further described with reference to the following non-limiting Examples with reference to the following drawings in which.

EXAMPLES

Experimental Procedure, Detection of Interleukin-8 (IL8)

Proximity-Probe Preparation

Figure 1:
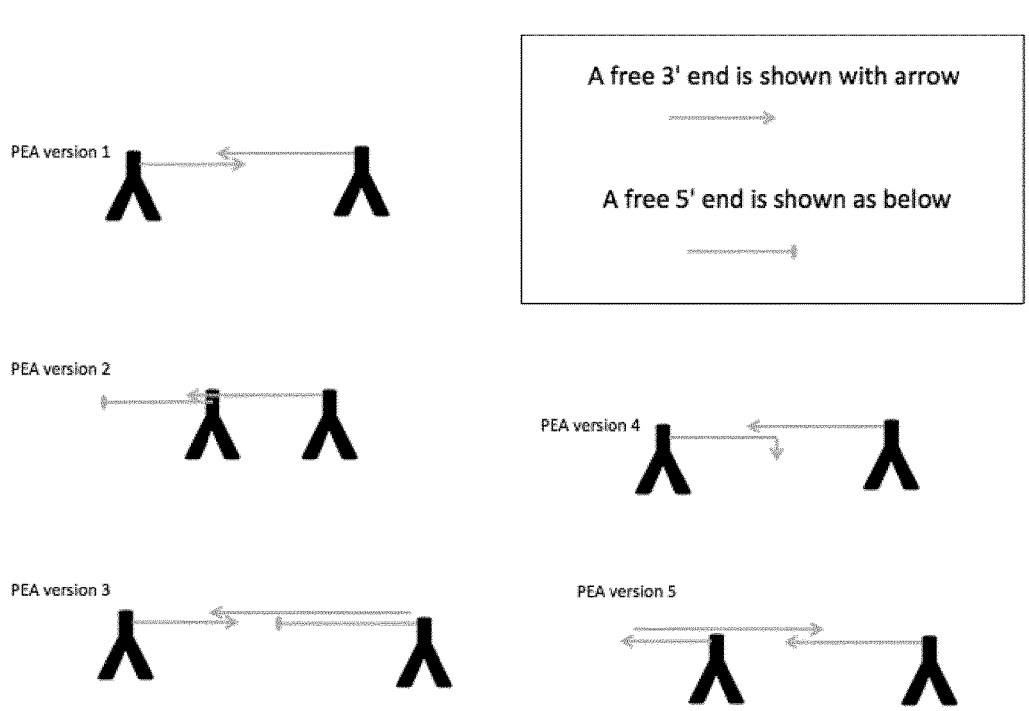
FIG. 1 shows a schematic representation of five different versions of proximity extension assays.

One batch of polyclonal antibody (RnD Systems, AF-208-NA) was coupled with Innovas Lightning-Link conjugation technology to two different ssDNA strands, one attached with the 5'-end:

(SEQ ID NO: 1)
5'-GGCCCAAGTGTTAATTTGCTTCACGATGAGACTGGATGAA-3' and the second one at the 3'-end:

(SEQ ID NO: 2)
5'-TCACGGTAGCATAAGGTGCAGTATGAGAACTTCGCTACAG-3'

A third oligonucleotide, referred to as "Extension oligo", was added to the 3'-attached conjugates at a 2:1 (oligo:conjugate) ratio.

PEA Protocol #1 (Two Step Version)

1 µL sample (PBS+0.1% BSA buffer, IL-8 antigen standard from RnD Systems 208-IL-010, EDTA plasma) was mixed with 1 µL blocking buffer containing 0.21 mg/ml goat IgG (Sigma Aldrich 19140), 107 µg/ml single stranded salmon sperm DNA (Sigma Aldrich D7656), 0.085% BSA, 4.3 mM EDTA, 0.21% Triton-X100, 0.02% sodium azide and 2.5 µM blocking conjugates (Olink AB, WO 2012/007511). Samples were blocked at 25° C. for 20 minutes.

To 2 µLs of the blocked samples 2 µL of probe mix (25 mM Tris-HCl, 4 mM EDTA, 1 mM Biotin, 0.016 mg/ml single stranded salmon sperm DNA (Sigma Aldrich D7656), 0.02% sodium azide and 100 pM of each PEA conjugate) was added and then incubated at 37° C. for 1 hour.

After the probe incubation the samples were transferred to a thermal cycler and put on hold at 37° C. 76 µL of dilution mix containing 70.5 mM Tris-HCl, 17.7 mM ammonium sulfate, 1.05 mM dithiothreitol and 40 µM (each) of dNTP's were added to the incubated samples. After 5 minutes at 37°

C. the second addition of 20 µL extension mix (66.8 mM Tris-HCl, 16.8 mM ammonium sulfate, 1 mM dithiothreitol, 33 mM magnesium chloride and 62.5 U/mL T4 DNA Polymerase (Fermentas, #EP0062)), or other DNA polymerases, were added. The extension reactions were performed at 37° C. for another 20 minutes and then heat inactivated at 80° C. for 10 minutes.

For the qPCR detection of extension products, 4 µL of the extension products were transferred to a qPCR plate and mixed with 6 µL qPCR mix (25 mM Tris-HCl, 7.5 mM magnesium chloride, 50 mM potassium chloride, 8.3 mM ammonium sulfate, 8.3% Trehalose (Acros Organics, 182550250), 333 µM (each) dNTP's, 1.67 mM dithiothreitol, 833 nM of each primer (forward: 5'-TCGTGAGC-CCAAGTGTTAATTTGCTTCACGA-3' (SEQ ID NO: 3), reverse: 5'-TGCAGTCTGTAGCGAAGTTCTCATACT-GCA-3' (SEQ ID NO: 4), Biomers), 417 nM Molecular Beacon (FAM-CCCGCTCGCTTATGCTACCGTGACCT-GCGAATCCCGAGCGGG-DABSYL, (SEQ ID NO: 5) Biomers), 41.7 U/mL recombinant Taq polymerase (Fermentas #EP0402) and 1.33 µM ROX reference (ROX-TTTTTTT, Biomers). Two step qPCR was run with initial denaturation at 95° C. for 5 minutes, followed by 45 cycles of 95° C. denaturation for 15 seconds and 60° C. combined annealing and extension for 1 minute.

Comparison of Different DNA Polymerases

Figure 2:
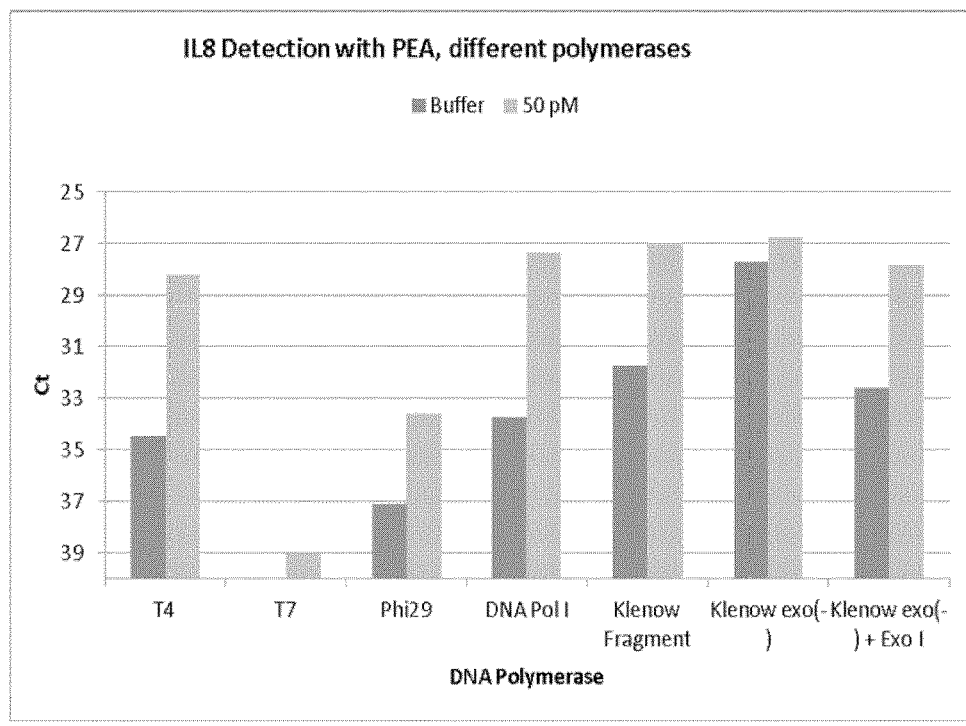
FIG. 2 is a bar chart showing the activity of various polymerases with 3' exonuclease activity or in combination with a 3' exonuclease in the detection of interleukin-8 (50 pM) using the methods of the invention.

When comparing a sample of DNA polymerases that have 3'→5' exonuclease activity (T4 DNA Polymerase, DNA Polymerase, Phi29 DNA Polymerase, DNA Polymerase I, Klenow Fragment) with those without (Klenow Fragment exo(−)), it was found there is a distinct difference in signal relative to the background, see FIG. 2. The Klenow Fragment without 3' exonuclease activity has a much higher background than the Klenow Frament (3' exo+), and if Exonuclease I is added to the Klenow Fragment exo(−) similar results to those using the Klenow fragment (3' exo+) were achieved. So exonuclease I, which is not a DNA polymerase, can rescue the reaction polymerized by Klenow (exo−).

Some DNA polymerases containing 3' exonuclease activity, e.g. T7 and phi-29 DNA polymerase, gave low signals both for background and antigen samples (FIG. 2). It is hypothesised that this result is a consequence of the strong 3' exonuclease activity found in these enzymes and further optimization of the specific reaction conditions for these enzymes would enable these enzymes to find utility in the methods described herein.

The positive effect of using an enzyme comprising 3' exonuclease activity in proximity extension assays is assumed arise from degradation of the free non-proximal DNA ends so that they can not accumulate extension products over time during the extension reactions itself.

Probe Incubation with Sephadex G-100 Beads

Figure 3:
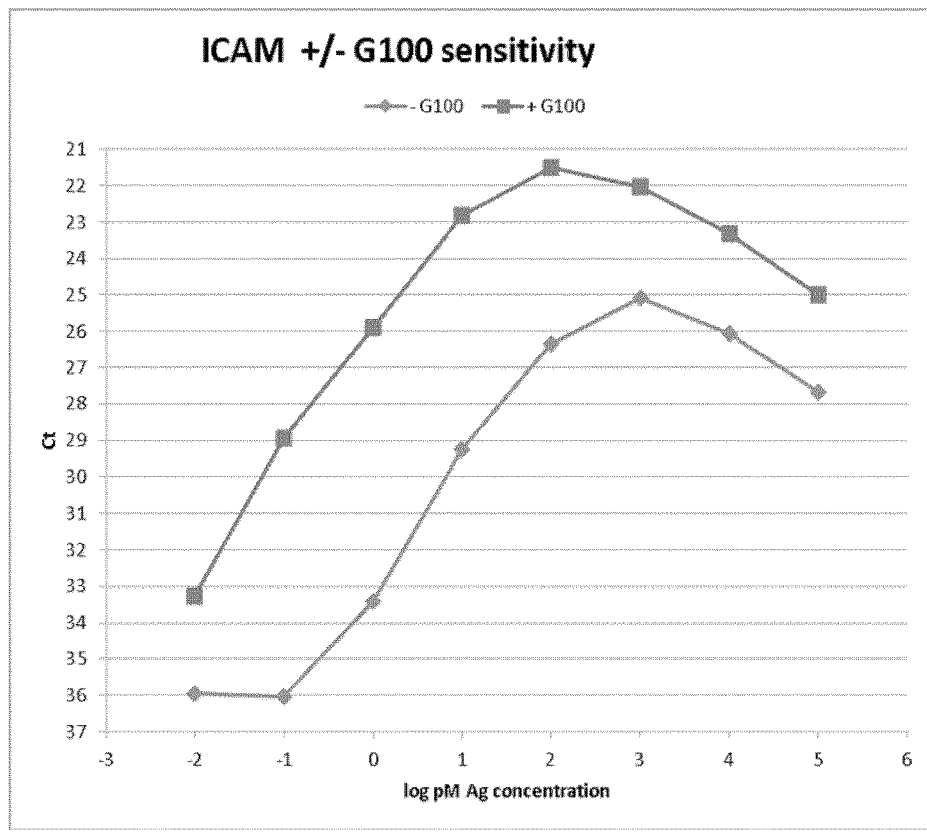
FIG. 3 shows a graph that plots the signal generated from the detection of an analyte (the ICAM antigen) in a sample using the methods of the invention in the presence and absence of a "crowding agent", sephadex G-100.

In order to investigate the possibility of enhancing PEA performance by the use of molecular crowding agents, e.g. crowding polymers, as suggested in US 20090162840 for proximity ligation assays, the use of sephadex beads was tested using the above described methods. Dry sephadex beads can upon rehydration in solution expand and by absorbing water, whilst larger molecules such as proteins (i.e. analytes) and proximity probes that may be present in the solution remain outside the beads. This effectively enhances the concentration of said proteins and proximity probes, thereby promoting target binding by said probes. FIG. 3 shows the results of an assay wherein 0.5 µg of sephadex G-100 was lyophilized at the bottom of the PEA incubation tubes onto which the probe mix and sample was added. Dramatic improvements in the sensitivity and signal to noise ratio are seen, indicating increased target binding.

Plasma Recovery and Matrix Effects on PEA

Figure 4:
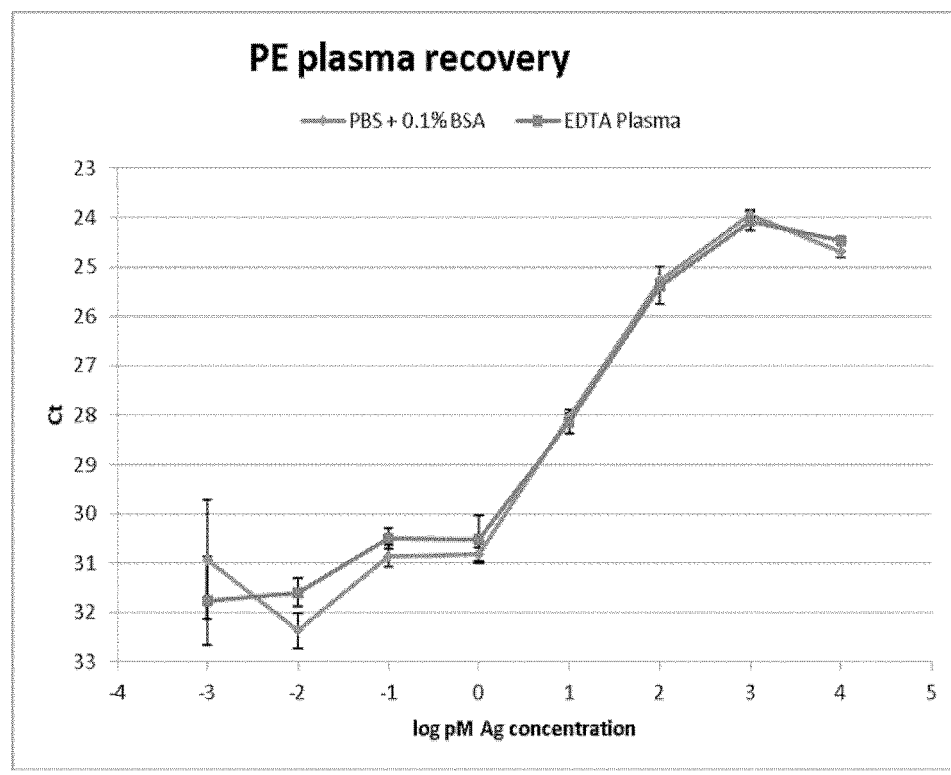
FIG. 4 shows graph that plots the signal generated from the detection of an analyte (phycoerythrin, PE) in a sample using the methods of the invention, where the analyte was added to either buffer or plasma.

To test the ability of PEA using 3' exonuclease efficient DNA polymerases to accurately detect proteins in a complex matrix, the assay described above were performed using human EDTA prepared plasma. The non-human protein phycoerythrin (PE) was spiked at various concentrations into either a non-complex matrix PBS (phosphate buffered saline) with 0.1% BSA, or a very complex matrix EDTA plasma and quantified by PEA. A non-human protein was selected so that recovery could be assessed even at low concentrations. Excellent recovery was observed for this analyte in plasma even at 10 pM (FIG. 4) as there was virtually no difference in signal between complex and non-complex matrix.

Figure 5:
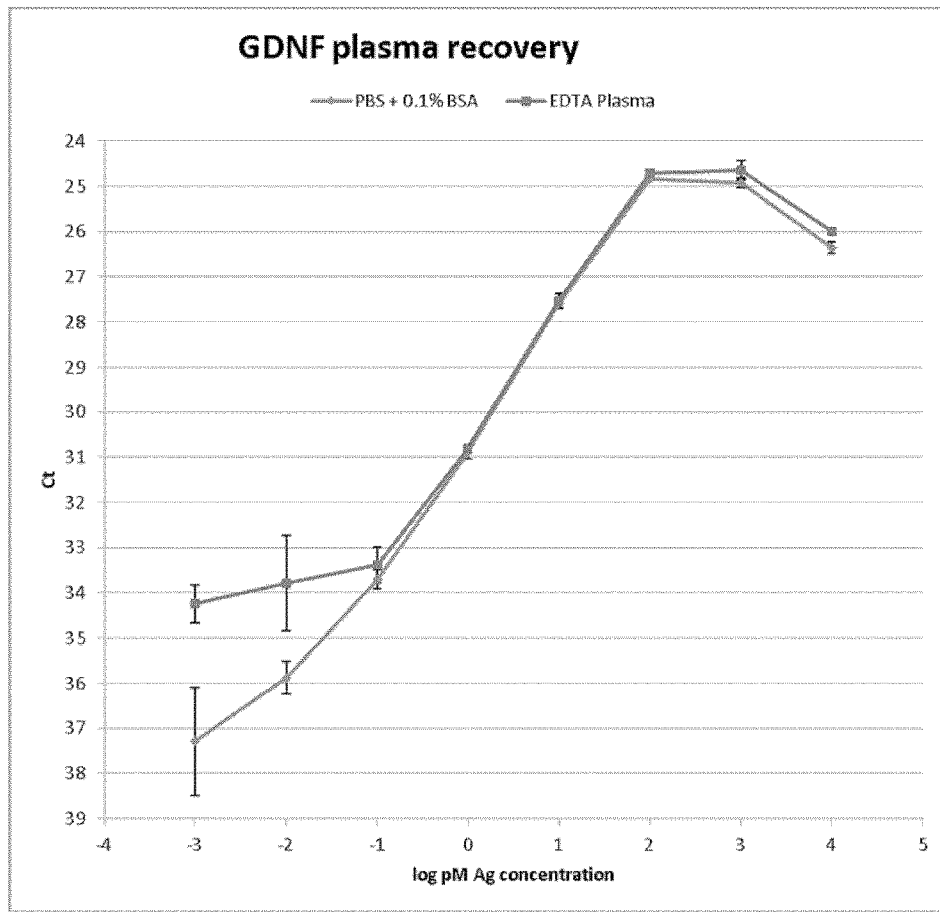
FIG. 5 shows graph that plots the signal generated from the detection of an analyte (Glial-cell Derived Neurotrophic Factor, GDNF) in a sample using the methods of the invention, where the analyte was added to buffer or naturally present in plasma.

In another example, the human protein GDNF (Glial-cell Derived Neurotrophic Factor) was spiked into human plasma, FIG. 5. This proteins is of very low abundance in plasma and difficult to detect with standard technologies. Again, outstanding recovery was observed for this analyte demonstrating that endogenous GDNF signal can be quantified at below 0.1 pM.

Simplified PEA Protocol (#2)

Figure 6:
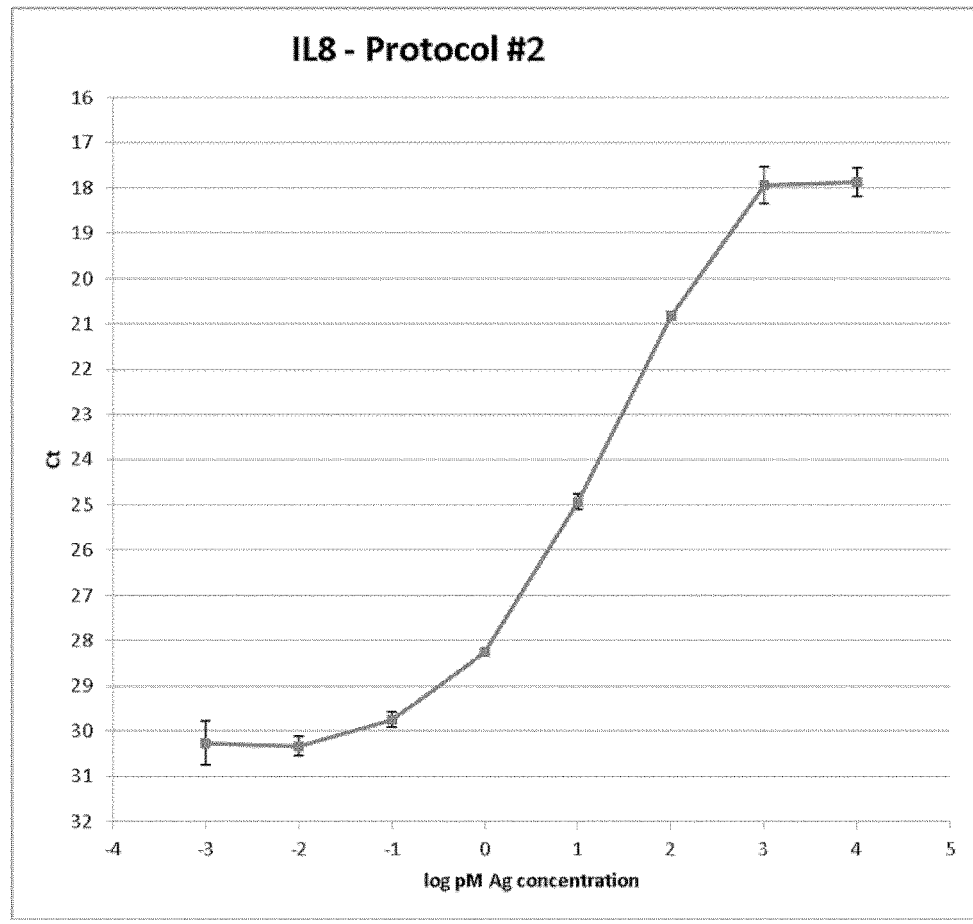
FIG. 6 shows graph that plots the signal generated from the detection of an analyte (Interleukin-8, IL8) in a sample using the "one step" method of the invention.
Figure 7:
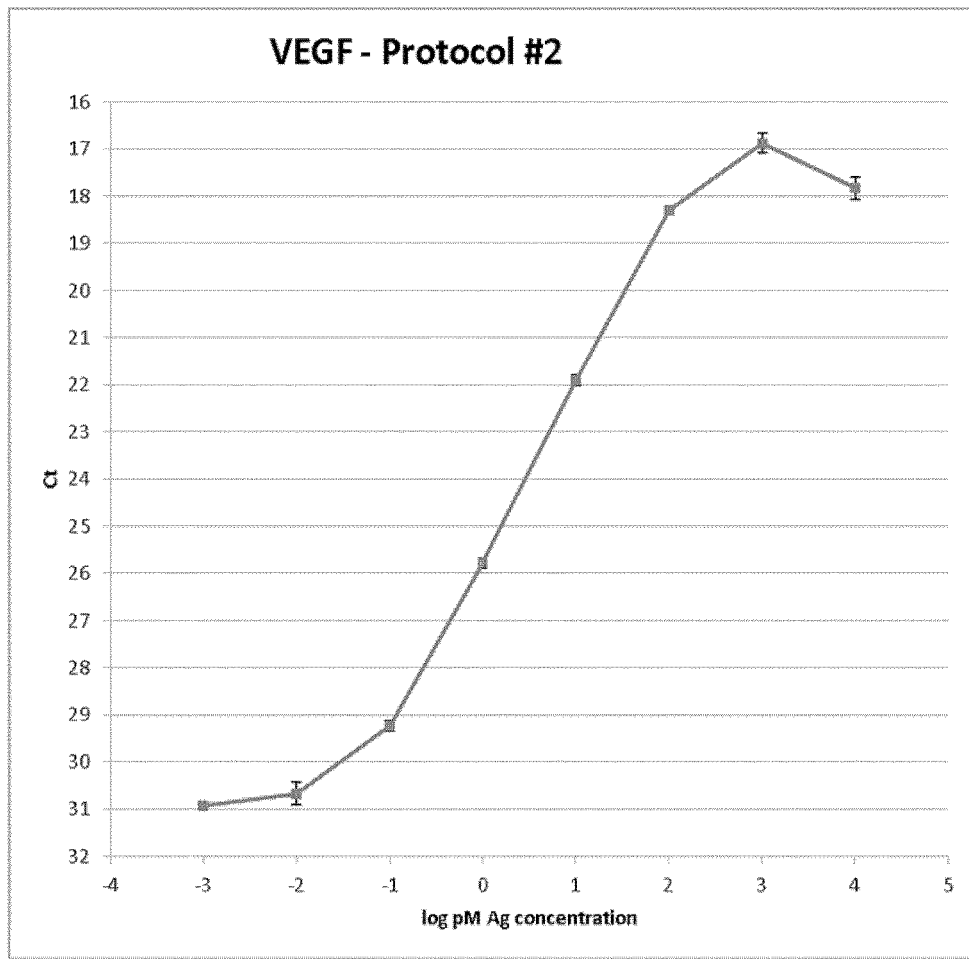
FIG. 7 shows graph that plots the signal generated from the detection of an analyte (Vascular endothelial growth factor, VEGF) in a sample using the "one step" method of the invention.
Figure 8:
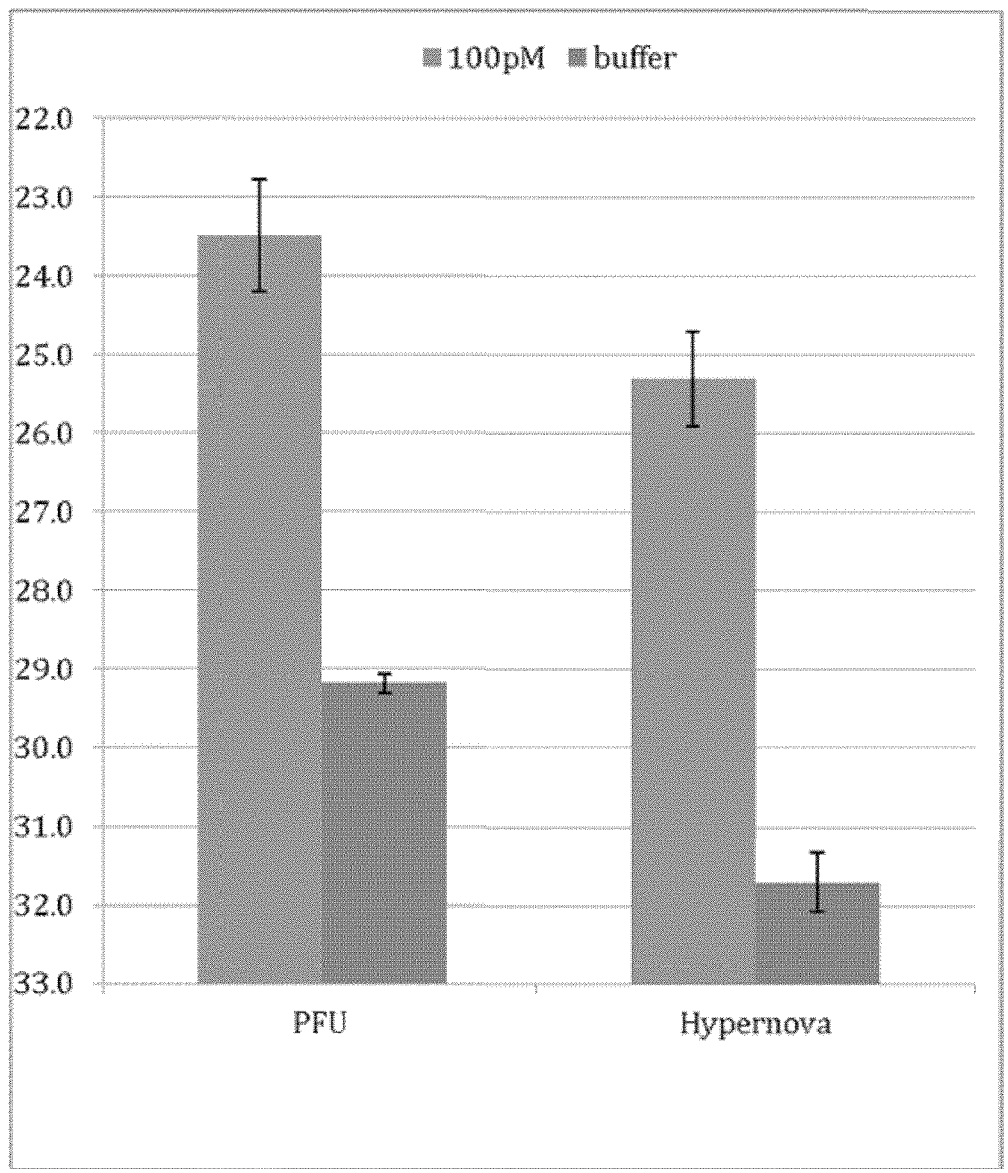
FIG. 8 shows a bar chart showing the activity of two hyperthermophilic polymerases with 3' exonuclease activity, namely Pfu DNA polymerase and Pwo DNA Polymerase (labelled as Hypernova™; the commercially available polymerase from DNA GDANSK) in the detection of interleukin-8 (100 pM) using the methods of the invention.

If there is a possibility to simplify experimental procedures, it is always desirable to do so. It was found that it was possible to combine the extension mix with the qPCR mix, making it possible to directly transfer the extension products from the thermal cycler to the qPCR instrument without any further pipetting and with less hands-on time. This protocol proved to retain a high sensitivity and signal along with good precision (FIGS. 6 and 7). In order to enable the use of a 3' exonuclease DNA polymerase for the proximity extension reaction in the presence of the qPCR primers, it was necessary to make said primers resistant to exonucleases. This was achieved by producing primers that form a hairpin structure at the lower temperature of the PEA reaction and modifying the last two residues at the 3'-end with phosphothioate. The one step version of the PEA protocol is set out below. The results for IL8 and VEGF detection are set out in FIGS. 6 and 7, respectively and obtained using the one step protocol.

PEA Protocol #2 (One Step Version)

1 µL sample (PBS+0.1% BSA buffer, IL-8 antigen standard from RnD Systems 208-IL-010, EDTA plasma) was mixed with 1 µL blocking buffer containing 0.19 mg/ml goat IgG (Sigma Aldrich 19140), 94 µg/ml single stranded salmon sperm DNA (Sigma Aldrich D7656), 0.075% BSA, 3.8 mM EDTA, 0.19% Triton-X100, 0.015% sodium azide and 2.5 µM blocking conjugates (Olink AB, WO 2012/007511). Samples were blocked at 25° C. for 20 minutes.

To 2 µLs of the blocked samples, 2 µL of probe mix (25 mM Tris-HCl, 4 mM EDTA, 1 mM Biotin, 0.016 mg/ml single stranded salmon sperm DNA (Sigma Aldrich D7656), 0.02% sodium azide and 100 pM of each PEA conjugate) was added and then incubated at 37° C. for 1 hour.

Following the probe incubation step, the samples were transferred to a thermal cycler and put on hold at 37° C. 36 µL of a dilution mix containing 1× iTaq SYBR Green Supermix (BioRad, 172-5851) and 3'-thioate protected hairpin primers (forward: 5'-TCGTGAGCCCAAGTGTTAATTTGCTTCAC*G*A-3' (SEQ ID NO: 6), reverse: TGCAGTCTGTAGCGAAGTTCTCATACTG*C*A-3' (SEQ ID NO: 7), * indicates thioate modifications) was added to the samples. After 3 minutes at 37° C., 10 µL of extension mix (1× iTaq SYBR Green Supermix (BioRad, 172-5851) and 62.5 U/mL T4 DNA Polymerase (Fermentas, #EP0062)) was added. The extension reactions were performed at 37° C. for another 20 minutes and then the T4 DNA polymerase was heat inactivated at 65° C. for 10 minutes.

The reaction mix (50 µL) contained the extension product and all of the reagents needed for qPCR. 10 µL of the reaction mix was transferred to an optical qPCR plate for quantification. Two step qPCR was run with initial denaturation at 95° C. for 5 minutes, followed by 45 cycles of 95° C. denaturation for 15 seconds and 64° C. combined annealing and extension for 1 minute.

The invention claimed is:

1. A method for detecting an analyte in a sample, comprising:
   (a) contacting said sample with one set or multiple sets of at least first and second proximity probes, which probes each comprise an analyte-binding domain and a nucleic acid domain and simultaneously bind to the analyte;
   (b) allowing the nucleic acid domains of the proximity probes to interact with each other upon binding of said proximity probes to said analyte, wherein said interaction comprises the formation of a duplex;
   (c) contacting said sample with a component comprising 3' exonuclease activity, wherein said component comprises a polymerase enzyme (c1) having 3' exonuclease activity and/or an exonuclease enzyme (c2) other than the polymerase enzyme (c1);
   (d) extending the 3' end of at least one nucleic acid domain of said duplex to generate an extension product, wherein the step may occur contemporaneously with or after step (c) and wherein the extension is performed by said polymerase (c1) or by a separate polymerase enzyme which is added during or after step (c);
   (e) amplifying the extension product;
   wherein amplifying the extension product comprises binding an amplification reagent to the extension product, wherein the amplification reagent is selected from the group consisting of:
      (i) a primer for the amplification;
      (ii) a padlock probe or circular oligonucleotide comprising a sequence which is complementary to an extended part of the extension product; and
      (iii) a template oligonucleotide which acts as a ligation template for circularization of an oligonucleotide comprising an extended part of the extension product; and
   wherein the amplification reagent is added before, at the same time or after the contacting step (c); and
   (f) detecting the amplified extension product.

2. The method of claim 1, wherein said detecting is quantitative.

3. The method of claim 1, wherein said detecting is qualitative.

4. The method of claim 1, wherein the analyte is a wholly or partially proteinaceous molecule and/or wherein the analyte binding domain of at least one of said at least first and second proximity probes is an antibody, or a binding fragment thereof or derivative thereof.

5. The method of claim 1, wherein the polymerase (c1) having 3' exonuclease activity comprises T4 DNA polymerase, T7 DNA polymerase, Phi29 (Φ29) DNA polymerase, DNA polymerase I, Klenow fragment of DNA polymerase I, *Pyrococcus furiosus* (Pfu) DNA polymerase and/or *Pyrococcus woesei* (Pwo) DNA polymerase.

6. The method of claim 1, wherein step (d) is carried out by an exo' nucleic acid polymerase with no or minimal 3' exonuclease activity.

7. The method of claim 6, wherein the exo' polymerase is added after the exonuclease enzyme (c2) wherein the sample is further incubated to allow the extension products to be generated and/or wherein the exo' polymerase is selected from the α subunit of DNA polymerase III, the Klenow exo(−) fragment of DNA polymerase I, Taq polymerase, Pfu (exo⁻) DNA polymerase and/or Pwo (exo⁻) DNA polymerase.

8. The method of claim 1, wherein the component comprising 3' exonuclease activity is exonuclease I and/or wherein the component comprising 3' exonuclease activity is inactivated prior to the step of amplifying the extension product.

9. The method of claim 8, wherein the 3' exonuclease activity is inactivated by heat denaturation.

10. The method of claim 9, wherein the heat inactivation is a first step of the amplification reaction of step (e).

11. The method of claim 1, wherein the amplification reagent is added to the sample before said sample is contacted with the component comprising 3' exonuclease activity or wherein the amplification agent is contacted with the sample contemporaneously with the component comprising 3' exonuclease activity.

12. The method of claim 11, wherein the amplification reagent is added between steps (b) and (c).

13. The method of claim 1, wherein step (e) comprises amplifying a portion of the extended part of the extension product.

14. The method of claim 13, wherein amplifying a portion of the extended part of the extension product is achieved using the primer and a second primer, such that the primers flank, respectively, sides of the portion of the extended part of the extension product.

15. The method of claim 13, wherein the amplification reagent is the template oligonucleotide.

16. The method of claim 15, wherein the amplification is rolling circle amplification.

17. The method of claim 1 wherein the amplification agent is the circular oligonucleotide.

18. The method of claim 1, wherein the amplification comprises a polymerase chain reaction.

19. The method of claim 18, wherein the polymerase chain reaction is a quantitative polymerase chain reaction.

20. The method of claim 19, wherein the quantitative polymerase chain reaction uses a dye which intercalates with nucleic acid molecules to provide a detectable signal.

21. The method of claim 20, wherein the dye which intercalates with nucleic acid molecules to provide a detectable signal is SYBR Green® or EvaGreen™.

22. The method of claim 18, wherein the primers used in the polymerase chain reaction are provided in a modified form such that they are resistant to 3' exonuclease activity.

23. The method of claim 22, wherein the primers comprise at least one modified nucleotide at the 3' end.

24. The method of claim 23, wherein the modified nucleotide is selected from any one or more of the group consisting of a thiophosphate-modified nucleotide, a locked nucleic acid nucleotide, a 2'-OMe-CE Phosphoramidite modified nucleotide, and a peptide nucleic acid nucleotide.

25. The method of claim 18, wherein primers are hotstart primers and/or wherein at least one of polymerases is a thermostable polymerase.

26. The method of claim 1, wherein one or both of the nucleic acid domains of the first and second proximity probes are extended in step (d) and/or wherein at least one of the nucleic acid domains is partially double stranded.

27. The method of claim 26, wherein at least one of the nucleic acid domains is a partially double stranded nucleic acid domain and comprises a single stranded nucleic acid domain hybridised to a splint oligonucleotide.

28. The method of claim 27, wherein prior to step (a) the splint oligonucleotide is pre-hybridised to the nucleic acid domain of a proximity probe and/or wherein the splint oligonucleotide is extended in step (d) to form an extension product.

29. The method of claim 28, wherein the extension product is circularized to provide a template for amplification.

30. The method of claim 29, wherein the 3' end of the extension product is ligated to the 5' end of the extension product oligonucleotide by a templated ligation.

31. The method claim 29, wherein said amplification is rolling circle amplification.

32. The method of claim 1, wherein a splint oligonucleotide is added to the sample before the proximity probes.

33. The method of claim 1, wherein a splint oligonucleotide is added to the sample at the same time as or after the proximity probes.

34. The method of claim 33, wherein the splint oligonucleotide is provided as the nucleic acid domain of a third proximity probe.

35. The method of claim 34, wherein the third proximity probe is added to the sample at the same time as said first and second proximity probes.

36. The method of claim 1, wherein the extended nucleic acid domains are ligated together.

37. The method of claim 36, wherein the ligation reaction is mediated by a splint oligonucleotide.

38. The method of claim 1, comprising multiplex analysis for detecting two or more analytes in a sample, said method comprising contacting the sample with multiple sets of at least first and second proximity probes, wherein each of the sets binds to one of the two or more analytes, and the nucleic acid domains of each set of the proximity probes interact with each other upon binding of said proximity probes to a respective analyte to form a duplex; extending the 3' end of at least one nucleic acid domain of each of the duplexes and generating a unique extension product for each of the sets; amplifying each of the unique extension products; and detecting the amplified unique extension products.

39. The method of claim 1, wherein a crowding agent is included in step (a) and/or (b).

40. The method of claim 39, wherein the crowding agent is sephadex, preferably wherein the sephadex is type G-100.

41. A method comprising multiplex analysis for detecting two or more analytes in a sample, comprising:
 (a) contacting the sample with multiple sets of at least first and second proximity probes, which probes each comprise an analyte-binding domain and a nucleic acid domain, wherein each of the sets binds to one of the two or more analytes;
 (b) for each set of proximity probes, allowing the nucleic acid domains of the proximity probes to interact with each other upon binding of said proximity probes to a respective analyte, wherein said interaction comprises the formation of a duplex;
 (c) contacting said sample with a component comprising 3' exonuclease activity, wherein said component comprises a polymerase enzyme (c1) having 3' exonuclease activity and/or an exonuclease enzyme (c2) other than the polymerase enzyme (c1);
 (d) extending the 3' end of at least one nucleic acid domain of each of the duplexes to generate a unique extension product for each of the sets, wherein the step may occur contemporaneously with or after step (c) and wherein the extension is performed by said polymerase (c1) or by a separate polymerase enzyme which is added during, or after step (c);
 (e) amplifying each of the unique extension products;
 wherein amplifying each of the extension products comprises allowing an amplification reagent to bind to an extended part of the extension product, wherein the amplification agent is selected from the group consisting of:
 (i) a primer for amplification;
 (ii) a padlock probe or circular oligonucleotide comprising a sequence which is complementary to an extended part of the extension product;

(iii) a template oligonucleotide which acts as a ligation template for circularization of an oligonucleotide comprising an extended part of the extension product; and wherein the amplification reagent is added before, at the same time or after the contacting step (c); and (f) detecting the amplified unique extension products.

42. The method of claim 41,
wherein the extension template for each of the extension products is linear.

43. The method of claim 41,
wherein either:
(i) the nucleic acid domains of the proximity probes are single-stranded and the nucleic acid domains of each set of proximity probes interact directly via regions of complementarity to each other; or
(ii) the nucleic acid domain of at least one of the proximity probes of each of the sets of proximity probes is partially double-stranded and comprises a single-stranded domain hybridized to a splint oligonucleotide, and the splint oligonucleotide is extended in step (d).

44. The method of claim 1
wherein the template for extension in step (d) is linear.

45. The method of claim 44, wherein the nucleic acid domains of each of the proximity probes are single-stranded and are attached to the analyte binding domain by their 5' ends, thereby leaving two free 3' ends which share a region of complementarity at their 3' ends and are able to interact by hybridization when the proximity probes are bound in proximity to their respective analyte binding targets on the analyte, and wherein at least one of the nucleic acid domains is extended using the nucleic acid domain of the other proximity probe to template extension.

46. The method of claim 44, wherein the nucleic acid domains of each of the proximity probes are single stranded, and wherein the nucleic acid domain of the first proximity probe is attached to the analyte-binding domain by its 5' end and the nucleic acid domain of the second proximity probe is attached to the analyte-binding domain by its 3' end, thereby leaving a free 3' end of the nucleic acid domain of the first proximity probe and a free 5' end of the nucleic acid domain of the second proximity probe, and wherein the 3' ends of the nucleic acid domains of the proximity probes share a region of complementarity at their 3' ends and are able to interact by hybridization when the proximity probes are bound to their respective analyte binding targets on the analyte, and wherein the nucleic acid domain of the first proximity probe is extended using the nucleic acid domain of the second proximity probe as a template.

47. The method of claim 44, wherein the nucleic acid domain of the first proximity probe is attached to the analyte-binding domain by its 5' end and the nucleic acid domain of the second proximity probe is attached to the analyte-binding domain by its 3' end, thereby leaving a free 3' end of the nucleic acid domain of the first proximity probe and a free 5' end of the nucleic acid domain of the second proximity probe, wherein the nucleic acid domains attached to the analyte binding domains do not have a region of complementarity, and wherein a third nucleic acid molecule is provided that has a region of complementarity with the nucleic acid domain of each proximity probe to allow the nucleic acid domains of the proximity probes to interact with each other by the third nucleic acid molecule hybridizing with the nucleic acid domains of the first and second proximity probes by hybridization when the proximity probes are bound to their respective analyte binding targets on the analyte, wherein the nucleic acid domain of the first proximity probe is extended using the third nucleic acid molecule as a template or wherein the third nucleic acid molecule is extended using the nucleic acid domain of the first proximity probe as a template.

48. The method of claim 44, wherein the nucleic acid domains of each of the proximity probes is single-stranded and are attached to the analyte binding domain by their 5' ends, thereby leaving two free 3' ends, wherein the 3' end of the first proximity probe comprises a sequence that is not fully complementary to the nucleic acid domain of the second proximity probe, wherein the nucleic acid domains are able to interact by hybridization when the proximity probes are bound in proximity to their respective analyte binding targets on the analyte, and wherein the 3' end of the nucleic acid domain of the first proximity probe is unable to hybridize to the second proximity probe, wherein at least the nucleic acid domain of the second proximity probe is extended using the nucleic acid domain of the first proximity probe as a template.

49. The method of claim 44, wherein the nucleic acid domain of each of the proximity probes is attached to the analyte binding domain by their 5' ends, thereby leaving two free 3' ends, wherein the nucleic acid domains attached to the analyte binding domains do not have a region of complementarity, and wherein a linear third nucleic acid molecule is provided that has a region of complementarity with the nucleic acid domain of each proximity probe to allow the nucleic acid domains of the proximity probes to interact with each other by the third nucleic acid molecule hybridizing with the nucleic acid domains of the first and second proximity probes when the proximity probes are bound to their respective analyte binding targets on the analyte, wherein the nucleic acid domain of the second proximity probe is extended using the third nucleic acid molecule as a template or wherein the third nucleic acid molecule is extended using the nucleic acid domain of the second proximity probe as a template.

50. The method of claim 1
wherein either:
(i) the nucleic acid domains of the proximity probes are single-stranded and interact directly via regions of complementarity to each other; or
(ii) the nucleic acid domain of at least one of the proximity probes is partially double-stranded and comprises a single-stranded domain hybridized to a splint oligonucleotide, and the splint oligonucleotide is extended in step (d).

51. The method of claim 39, wherein the crowding agent is sephadex is type G-100.

52. The method of claim 1, wherein the amplification of step (e) is performed using a different polymerase than the polymerase enzyme (c1) having 3' exonuclease activity that is used in step (d) for extension.

* * * * *